(12) United States Patent
Binder et al.

(10) Patent No.: US 10,413,379 B2
(45) Date of Patent: Sep. 17, 2019

(54) REDUCED PRESSURE WOUND THERAPY KIT AND PACKAGING

(71) Applicant: Smith & Nephew PLC, Watford, Hertfordshire (GB)

(72) Inventors: Ian Binder, Chippenham (GB); Sarah Jenny Collinson, Hull (GB); John Cowan-Hughes, Bristol (GB); John Gowans, Hessle (GB); Beverley Love, Hessle (GB); David Patterson, Bromborough (GB); Mark Russell, Roos (GB); Peter Sleight, Cottingham (GB); Philip Walsh, Bristol (GB)

(73) Assignee: Smith & Nephew PLC, Watford (GB)

( * ) Notice: Subject to any disclaimer, the term of this patent is extended or adjusted under 35 U.S.C. 154(b) by 98 days.

(21) Appl. No.: 15/311,805

(22) PCT Filed: May 15, 2015

(86) PCT No.: PCT/EP2015/060757
§ 371 (c)(1),
(2) Date: Nov. 16, 2016

(87) PCT Pub. No.: WO2015/173389
PCT Pub. Date: Nov. 19, 2015

(65) Prior Publication Data
US 2017/0119487 A1    May 4, 2017

Related U.S. Application Data

(60) Provisional application No. 61/994,782, filed on May 16, 2014.

(51) Int. Cl.
*A61B 50/33* (2016.01)
*A61M 1/00* (2006.01)
(Continued)

(52) U.S. Cl.
CPC .............. *A61B 50/33* (2016.02); *A61B 50/30* (2016.02); *A61M 1/0088* (2013.01);
(Continued)

(58) Field of Classification Search
CPC ...... A61B 50/33; A61B 50/30; A61M 1/0088; B65D 75/14; B65D 75/36; B65D 75/527; B65D 75/54
(Continued)

(56) References Cited

U.S. PATENT DOCUMENTS

| D134,249 S | 11/1942 | Button |
| 2,874,707 A | 2/1959 | Koppel |

(Continued)

FOREIGN PATENT DOCUMENTS

| CN | 1976849 | 6/2007 |
| CN | 201907705 | 7/2011 |

(Continued)

OTHER PUBLICATIONS

International Search Report and Written Opinion, re PCT Application No. PCT/EP2015/060757, dated Jul. 6, 2015.
(Continued)

*Primary Examiner* — Steven A. Reynolds
*Assistant Examiner* — Javier A Pagan
(74) *Attorney, Agent, or Firm* — Knobbe, Martens, Olson & Bear LLP

(57) ABSTRACT

Disclosed herein are several embodiments of medical device packaging, and more particularly to a reduced pressure therapy kit and packaging and methods of using the same in the treatment of wounds. Some embodiments are directed towards packaging including a dressing compartment for storing wound dressings and having use instructions printed thereon, the dressing compartment detachably connected to a pump compartment for storing a sterile pump. After
(Continued)

removal of the pump, the pump compartment can be detached from the dressing compartment and discarded. The dressing compartment can be retained together with any additional dressings and the use instructions.

19 Claims, 43 Drawing Sheets

(51) Int. Cl.
| | | |
|---|---|---|
| *A61B 50/30* | (2016.01) | |
| *B65D 75/14* | (2006.01) | |
| *B65D 75/36* | (2006.01) | |
| *B65D 75/52* | (2006.01) | |
| *B65D 75/54* | (2006.01) | |
| *A61B 50/00* | (2016.01) | |

(52) U.S. Cl.
CPC ............ *B65D 75/14* (2013.01); *B65D 75/36* (2013.01); *B65D 75/527* (2013.01); *B65D 75/54* (2013.01); *A61B 2050/0065* (2016.02); *A61B 2050/3008* (2016.02); *A61M 1/0023* (2013.01); *A61M 2209/06* (2013.01)

(58) Field of Classification Search
USPC .......................................................... 206/570
See application file for complete search history.

(56) References Cited

U.S. PATENT DOCUMENTS

| | | |
|---|---|---|
| 3,640,379 A | 2/1972 | Weingarden |
| 3,972,328 A | 8/1976 | Chen |
| D254,219 S | 2/1980 | Papciak |
| D267,834 S | 2/1983 | Yew |
| D268,098 S | 3/1983 | Brown |
| D275,425 S | 9/1984 | Briggs |
| D281,836 S | 12/1985 | Sparkman |
| D289,461 S | 4/1987 | Humphries |
| 4,977,483 A | 12/1990 | Perretta |
| D313,505 S | 1/1991 | Leopoldi et al. |
| D316,181 S | 4/1991 | Clifton |
| D320,308 S | 10/1991 | Whitworth |
| D327,363 S | 6/1992 | Farb |
| 5,238,732 A | 8/1993 | Krishnan |
| D339,287 S | 9/1993 | Levin |
| 5,344,024 A | 9/1994 | Cohu |
| D365,754 S | 1/1996 | Plassier |
| D369,295 S | 4/1996 | Kobari et al. |
| 5,549,584 A | 8/1996 | Gross |
| D389,639 S | 1/1998 | Priebe |
| D393,591 S | 4/1998 | Baryshyan |
| 5,759,570 A | 6/1998 | Arnold |
| D396,750 S | 8/1998 | Slater et al. |
| D397,869 S | 9/1998 | Minhas |
| D398,527 S | 9/1998 | Maceachern et al. |
| 5,894,923 A | 4/1999 | Hamstra et al. |
| D409,752 S | 5/1999 | Bishay et al. |
| D420,586 S | 2/2000 | Maceachern et al. |
| D431,902 S | 10/2000 | Mellin |
| D455,312 S | 4/2002 | Myszka et al. |
| 6,626,891 B2 | 9/2003 | Ohmstede |
| 6,913,149 B2 | 7/2005 | Gelardi et al. |
| D537,735 S | 3/2007 | Fountoulakis |
| D566,773 S | 4/2008 | Delmotte et al. |
| 7,361,184 B2 | 4/2008 | Joshi |
| 7,381,859 B2 | 6/2008 | Hunt et al. |
| D573,458 S | 7/2008 | Anderson et al. |
| D579,195 S | 10/2008 | Kagawa |
| D589,798 S | 4/2009 | Liipola |
| 7,569,742 B2 | 8/2009 | Haggstrom et al. |
| 7,615,036 B2 | 11/2009 | Joshi et al. |
| D606,394 S | 12/2009 | Stewart |
| D607,717 S | 1/2010 | Hodges |
| 7,699,823 B2 | 4/2010 | Haggstrom et al. |
| D618,546 S | 6/2010 | Easterbrook et al. |
| D618,810 S | 6/2010 | Tanigawa et al. |
| D621,125 S | 8/2010 | Heintzelman |
| 7,775,998 B2 | 8/2010 | Riesinger |
| 7,811,269 B2 | 10/2010 | Boynton et al. |
| D627,789 S | 11/2010 | Jewitt et al. |
| 7,846,141 B2 | 12/2010 | Weston |
| 7,910,791 B2 | 3/2011 | Coffey |
| 7,922,703 B2 | 4/2011 | Riesinger |
| D637,298 S | 5/2011 | Vaisnys et al. |
| 7,964,766 B2 | 6/2011 | Blott et al. |
| D644,514 S | 9/2011 | Robins |
| D645,735 S | 9/2011 | Clark et al. |
| 8,074,803 B2 | 12/2011 | Motsch et al. |
| D661,188 S | 6/2012 | Fahy |
| D661,189 S | 6/2012 | Fahy |
| D661,190 S | 6/2012 | Fahy |
| D663,315 S | 7/2012 | Cielak et al. |
| D663,944 S | 7/2012 | Bouskill |
| D667,020 S | 9/2012 | MacKenzie et al. |
| D668,948 S | 10/2012 | LaTrobe |
| D675,739 S | 2/2013 | McCormack |
| D678,067 S | 3/2013 | Jones et al. |
| D680,131 S | 4/2013 | Anzures |
| D682,279 S | 5/2013 | Fuchs |
| D686,735 S | 7/2013 | Tsuruta et al. |
| D687,300 S | 8/2013 | Jones et al. |
| D690,425 S | 9/2013 | Heinecke et al. |
| D692,146 S | 10/2013 | Mochizuki et al. |
| D697,925 S | 1/2014 | Woo-Seok et al. |
| 8,631,935 B2 | 1/2014 | Tomes et al. |
| D699,363 S | 2/2014 | Mochizuki et al. |
| D699,856 S | 2/2014 | Mochizuki et al. |
| D704,442 S | 5/2014 | Chen |
| D707,828 S | 6/2014 | Ehninger et al. |
| D708,055 S | 7/2014 | Elston et al. |
| D709,205 S | 7/2014 | Ehninger et al. |
| D723,792 S | 3/2015 | Anderson et al. |
| D724,620 S | 3/2015 | Hansen et al. |
| D729,515 S | 5/2015 | Slimane |
| D730,728 S | 6/2015 | Fath |
| D740,304 S | 10/2015 | MacLean |
| D742,900 S | 11/2015 | Seo et al. |
| 9,241,873 B2 | 1/2016 | Upchurch et al. |
| D750,478 S | 3/2016 | Kiss |
| D754,732 S | 4/2016 | Yoon et al. |
| D756,380 S | 5/2016 | Kwon |
| D758,851 S | 6/2016 | Binder et al. |
| D759,063 S | 6/2016 | Chen |
| D759,116 S | 6/2016 | Dellinger |
| D761,023 S | 7/2016 | Tramontana |
| D766,713 S | 9/2016 | Kiss |
| D806,541 S | 1/2018 | Love et al. |
| D818,813 S | 5/2018 | Love et al. |
| 2003/0230509 A1 | 12/2003 | Fitzgerald et al. |
| 2007/0225663 A1 | 9/2007 | Watt et al. |
| 2008/0306456 A1 | 12/2008 | Riesinger |
| 2009/0108010 A1 | 4/2009 | Ludden-Biegel |
| 2010/0274205 A1* | 10/2010 | Morelli ............... A61M 1/0088 604/290 |
| 2011/0036735 A1 | 2/2011 | Cho |
| 2011/0315754 A1 | 12/2011 | Gao |
| 2012/0072870 A1 | 3/2012 | Akifusa |
| 2013/0110058 A1* | 5/2013 | Adie .................... A61M 1/0031 604/319 |
| 2013/0186511 A1* | 7/2013 | Hess ..................... A61M 5/008 141/1 |
| 2014/0079342 A1 | 3/2014 | Kiiskinen |
| 2015/0076025 A1 | 3/2015 | Wilmers et al. |

FOREIGN PATENT DOCUMENTS

| | | |
|---|---|---|
| EP | 0 913 164 | 5/1999 |
| FR | 1 163 907 | 10/1958 |
| FR | 2 644 341 | 9/1990 |
| WO | WO 2004/028313 | 4/2004 |

(56) References Cited

FOREIGN PATENT DOCUMENTS

| WO | WO 2007/138160 | 12/2007 |
|---|---|---|
| WO | WO 2015/173389 | 11/2015 |

OTHER PUBLICATIONS

Internetmed, "Used Smith & Nephew 4297 Orthopedic Offset Drill Guide Power Instruments," listing No. 234150974, posted Apr. 4, 2015, printed Oct. 27, 2015. http://internetmed.com/product/used-smith-nephew-4297-orthopedic-offset-drill-guide-power-instruments.

Kendall ULTEC Hydrocolloid Dressing (4"×4"), product ordering page, web page downloaded Jul. 13, 2014.

Packaging for Pico Single Use Negative Pressure Wound Therapy System (2012) in 1 page.

Protz, Kerstin: "Modern Wundauflagen unterstutzen Heilungsprozess", Wundversorgung: Indikation und Anwendung, Geriatrie Journal, Apr. 2005, pp. 3333-3339, with translation.

Smith & Nephew, "PICO packaging reduction", Jun. 2014, http://www.smith-nephew.com/news-and-media/case-studies/picosntm-packaging-reduction/.

International Preliminary Report on Patentability, re PCT Application No. PCT/EP2015/060757, dated Dec. 1, 2016.

Adventure Medical Kits, "Adventure Medical Kits Professional Trauma Pak First Aid Kit with QuikClot", announced Oct. 2011, accessed online Aug. 22, 2017, in 8 pages. URL: http://www.amazon.com.

Cederroth, "Cederroth 1910 4-in-1 Bloodstopper Dressing", announced Jul. 2011, accessed online Aug. 22, 2017, in 6 pages. URL: http://www.amazon.com.

Internetmed, "Used Smith & Nephew 4297 Orthopedic Offset Drill Guide Power Instruments," listing No. 234150974, posted Apr. 4, 2015, printed Jul. 23, 2015, in 2 pages. URL: http://internetmed.com/product/used-smith-nephew-4297-orthopedic-offset-drill-guide-power-instruments.

Philips, "Pediatric, Infant, Child Pads OnSite & Home AED", announced Sep. 2012, accessed online Aug. 22, 2017, in 7 pages. URL: http://www.amazon.com.

Smith & Nephew, "PICO Single Use Negative Pressure Wound Therapy System", spiral booklet, Mar. 2011, in 7 pages.

\* cited by examiner

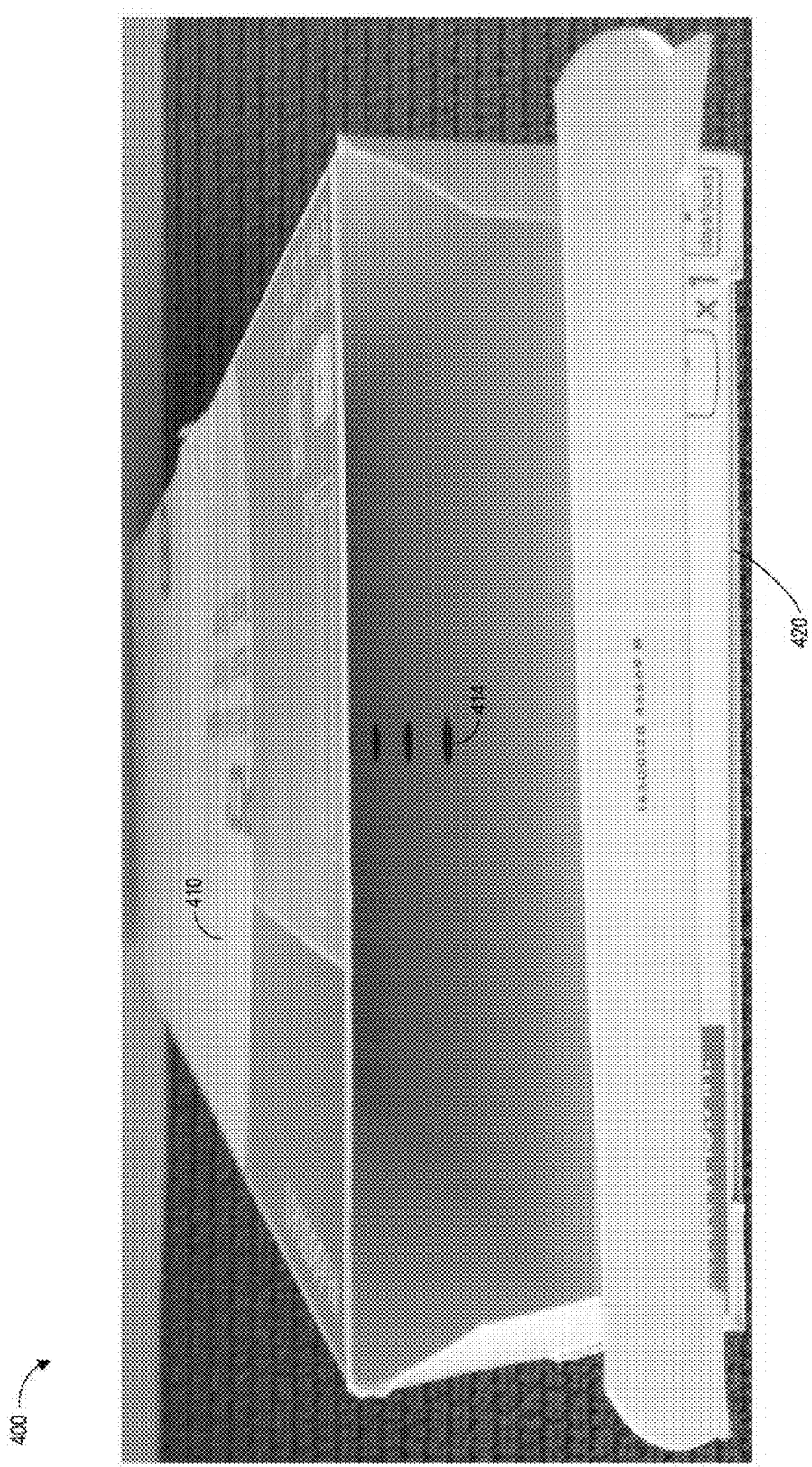

REDUCED PRESSURE WOUND THERAPY KIT AND PACKAGING

CROSS REFERENCE TO RELATED APPLICATIONS

This application is a national stage application of International Patent Application No. PCT/EP2015/060757, filed on May 15, 2015, which claims the benefit of U.S. Provisional Application Ser. No. 61/994,782, filed May 16, 2014, the entirety of which is hereby incorporated by reference.

BACKGROUND

Technical Field

Embodiments disclosed herein relate to packaging for medical devices. For example but without limitation, some embodiments disclosed herein relate to packaging for devices used to treat a wound with reduced pressure.

Description of the Related Art

The treatment of open or chronic wounds that are too large to spontaneously close or otherwise fail to heal by means of applying negative or reduced pressure to the site of the wound is well known in the art. Negative pressure wound therapy (NPWT) or topical negative pressure (TNP) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines bacteria.

Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Many different types of wound dressings are known for aiding in NPWT systems. These different types of wound dressings include many different types of materials and layers, for example, gauze, pads, foam pads or multi-layer wound dressings. The wound dressing may be sealed to a suction port providing connection to a length of tubing, which may be used to pump fluid out of the dressing and also to transmit negative pressure from a pump to the wound dressing.

In certain NPWT dressings, an absorbent, gentle-adhesive wound dressing may be sealed over a wound and connected to a source of negative pressure such as a portable vacuum pump. The connection may be a fluidic connector pre-attached to the dressing. The dressing may be configured to absorb fluid from the wound and to distribute negative pressure across the wound bed. When the dressing has reached its absorbent capacity, it may be removed and a new dressing may be sealed over the wound and attached to the negative pressure source. Although this may be carried out by medical staff in a hospital setting, certain NPWT systems are sold to patients for at-home use. Known packaging of a NPWT system have included boxes and trays having one or more compartments to receive components such as a negative pressure pump, wound dressings, tubing, batteries and an instruction manual. However, such prior art packaging serves little or no purpose to the user after the components have been removed from the packaging.

SUMMARY OF SOME EMBODIMENTS

Some embodiments disclosed herein are directed toward medical device packaging and methods of use. For example, medical device packaging as described herein may be utilized to house components of a negative pressure wound therapy system that may include, for example, one or more wound dressings and a negative pressure pump. In some embodiments, the packaging may also include instructions provided directly on the packaging that may be utilized by the user of the medical device. In some embodiments, the packaging may be designed such that a first portion of the packaging is removable or detachable from a second portion of the packaging. The first portion may be disposed by a user while the second portion may be retained and be used to contain any unused components of the medical device. The instructions provided on the packaging may be provided directly onto a surface of the second portion, such as by printing or applying a label thereto.

In some embodiments, the medical device may comprise a negative pressure wound therapy system including one or more dressings and a negative pressure pump, which together with packaging forms a negative pressure wound therapy kit. A first portion of packaging may be utilized to contain the negative pressure pump, and a second portion of the packaging may be utilized to contain one, two or more wound dressings. In some embodiments, the first portion may also be utilized to contain an instruction manual, batteries and/or connectors or tubes to connect the wound dressing to the negative pressure pump. The second portion may be utilized to retain any unused wound dressings after a first wound dressing is used. The first portion may be removable or detachable from the second portion so that the first portion can be disposed and the second portion retained by the user. The second portion can include instructions provided directly onto a surface of the second portion, that may be used by a user applying and/or operating the components of the negative pressure wound therapy system.

In one embodiment, a medical device packaging system comprises:

a first compartment configured to contain a first portion of the device, the first compartment defined by a bottom panel, an upper panel, and at least one sidewall;

a second compartment configured to contain a second portion of the device, the second compartment defined by a bottom panel, an upper panel, and at least one sidewall; and instructions for using the medical device provided on an exterior surface of the upper panel of the second compartment; and wherein the first compartment is removably connected to the second compartment in a hinged manner allowing the first compartment and second compartment to be folded together such that the upper panel of the second compartment faces the upper panel of the first compartment; and wherein removal of the first compartment from the second compartment allows a user to discard the first compartment and retain the second compartment including the instructions for using the medical device.

In some embodiments, the medical device packaging system of claim can further comprise a fold line in a rear sidewall of the first compartment, wherein the fold line is adapted to provide the hinged manner allowing the first compartment and second compartment to be folded apart. The fold line can comprise a number of perforations adapted to allow removal of the first compartment from the second compartment. The fold line can comprise a weakened line adapted to allow removal of the first compartment from the second compartment. The instructions provided on the exterior surface of the upper panel of the second compartment may be visible when the first compartment and second compartment are folded apart. The instructions provided on the exterior surface of the upper panel of the second compartment may be concealed when the first compartment and second compartment are folded together.

In some embodiments, the upper panel of the first compartment can comprise at least one opening adapted to form a recess for receiving and supporting a tray containing the first portion of the device. The medical device packaging system can further comprise the tray containing the first portion of the device. The at least one opening in the upper panel of the first compartment may be visible when the first compartment and second compartment are folded apart. The at least one opening in the upper panel of the first compartment may be concealed when the first compartment and second compartment are folded together.

In some embodiments, the first compartment may be configured to contain one or more wound dressings and the second compartment may be configured to contain a pump. The first compartment may contain one or more wound dressings and the second compartment may contain a pump.

In another embodiment, a negative pressure wound therapy device packaging system comprises:
a first compartment configured to contain a negative pressure pump, the first compartment defined by a bottom panel, an upper panel, and at least one sidewall;
a second compartment configured to contain a plurality of wound dressings, the second compartment defined by a bottom panel, an upper panel, and at least one sidewall; and
instructions for using the negative pressure device provided on an exterior surface of the upper panel of the second compartment;
wherein the first compartment is removably connected to the second compartment in a hinged manner (i) allowing the first compartment and second compartment to be folded together such that the upper panel of the second compartment faces the upper panel of the first compartment, and (ii) allowing the first compartment and second compartment to be unfolded such that the negative pressure pump contained in the first compartment can be removed from the first compartment; and
wherein removal of the first compartment from the second compartment allows a user to discard the first compartment and retain the second compartment including the instructions for using the negative pressure device together with any unused wound dressings.

In some embodiments, the upper panel of the first compartment comprises at least one opening adapted to form a recess for receiving and supporting a tray. The negative pressure wound therapy device packaging system may further comprise the tray, the tray comprising: a rim extending around the perimeter of the tray adapted to rest against a portion of an exterior surface of the upper panel of the first compartment, the portion of the exterior surface of the upper panel of the first compartment surrounding the at least one opening; and a recessed tray portion extending downwardly from the rim, the recessed tray portion adapted to receive and support at least the negative pressure pump, the recessed tray portion sized and shaped to fit within the at least one opening in the upper panel of the first compartment. The tray may further comprise at least one additional recessed tray portion extending downwardly from the rim and adapted to receive and support at least one battery for the negative pressure pump. The tray may further comprise an additional recessed tray portion extending downwardly from the rim and connected to the recessed tray portion, the additional recessed tray portion adapted to receive and support a length of conduit tubing connected to the negative pressure pump. The negative pressure wound therapy device packaging system may further comprise a pump contained in the first compartment and one or more wound dressings contained in the second compartment.

In another embodiment, medical device packaging comprises:
a first portion and a second portion, wherein the first portion is removable or detachable from the second portion so that the first portion may be disposed by a user while the second portion may be retained and be used to contain any unused components of the medical device; and
instructions provided on a surface of the second portion that may be utilized by the user of the medical device.

BRIEF DESCRIPTION OF THE DRAWINGS

Embodiments of the present invention will now be described hereinafter, by way of example only, with reference to the accompanying drawings in which like numbers are used to denote like features.

DETAILED DESCRIPTION OF THE PREFERRED EMBODIMENTS

I. Introduction

Certain embodiments disclosed herein relate to negative or reduced therapy kit packaging including a detachable, book-format carton and instruction images printed on the carton. Two separate compartments, one configured to store one or more dressings and optionally any attached or separate fluidic connectors (referred to herein as a "dressing compartment"), and the other configured to store a negative pressure pump (referred to herein as a "pump compartment"), may be attached in a book format or hinged manner. The spine for the carton may be perforated to allow a user to easily separate the two compartments as desired. A user may open the packaging by unfolding the two compartments away from each other while they remain connected to each other, and the user may also open each compartment to remove the contents. On an inside panel of the dressing compartment may be printed instructions for using the system.

For example, the pump in the pump compartment and a dressing and fluidic connector from the dressing compartment can be removed and used to perform a treatment on a patient. Once the pump has been removed, the pump compartment may no longer be necessary, so it can be separated from the dressing compartment and be discarded. The dressing compartment, however, may be retained as it includes the operating instructions printed thereon, and it also may include one or more additional dressings for use with the pump should another dressing be needed or desired. The dressing compartment can include one or more through holes or viewing windows for determining whether any unused dressings are left.

Advantageously, this design allows the user to retain a smaller size package for any remaining unused dressing(s). The design also provides improved communication with the user by printing instructions on a surface of the package that will be retained with the unused dressing(s).

II. Overview of Example Kits and Packaging

Figure 1:
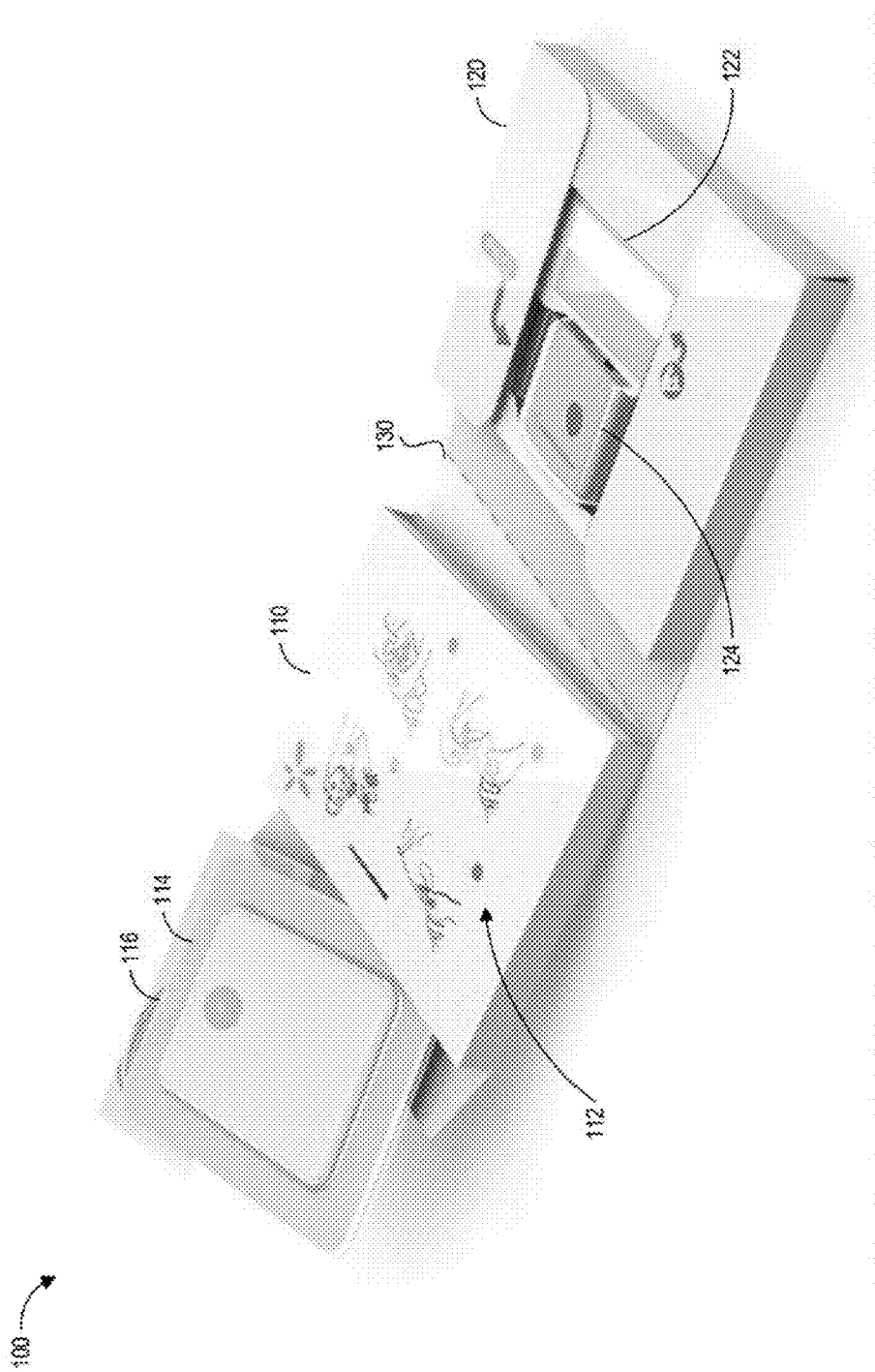
FIG. 1 illustrates an embodiment of a reduced pressure wound therapy kit including packaging, a pump, a dressing, a conduit and one or more batteries.

FIG. 1 illustrates an embodiment of a reduced pressure wound therapy kit 100 including packaging having a dressing compartment 110 for storage of dressings 114 and a pump compartment 120 for storage of a pump 124. Either compartment may store one or more conduits and/or connectors used to connect the dressing to the pump. As illustrated, a conduit 116 may be provided in the dressing compartment 110. One or more batteries may also be stored in the second compartment 120. In one non-limiting embodiment, each compartment may comprise one or more panels, for example a bottom panel and an upper panel that are separated by one or more sidewalls to define an inner volume to receive components of the system therein.

For example. the dressing compartment 110 can be a reclosable carton compartment configured to store one or more dressings and any attached or separate fluidic connectors, ports, or conduits 116. The dressing compartment may comprise an upper panel, a bottom panel and three sidewalls enclosing an inner volume to receive one or more dressings. An opening may be provided into the inner volume, the opening being closable with a flap that may fold over the opening having a tab insertable into a slot in the upper panel. Graphical and/or textual use instructions 112 can be provided (such as by printing) on a surface of the dressing compartment 110, for example on the upper panel such as shown in FIG. 1. When folded together with the pump compartment 120, the exterior surface of the dressing compartment 110 depicting the instructions 112 can be concealed by the pump compartment 120, however when the compartments 110, 120 are folded open to access the pump 124 the exterior surface of the dressing compartment 110 depicting the instructions 112 can face the user.

Because the dressing compartment 110 can be opened and closed and retained for storage of any unused dressings, in some embodiments each dressing 114 may be individually sealed, together with any preattached fluidic connectors, ports, or conduits, in sterile packaging before placement in the dressing compartment 110. In other embodiments, dressing compartment 110 may have a number of individually openable, sealed compartments containing the dressings and any preattached fluidic connectors, ports, or conduits. Accordingly, any unused dressings 114 can remain sterile even after the clinician or user initially opens the dressing compartment 110 to remove a first dressing.

As described in International Patent Application No. PCT/IB2013/002060, which disclosure is hereby incorporated by reference as if fully set forth herein, the wound dressing 114 can include any of a number of layers including a cover layer, a masking layer, an absorbent layer, an acquisition distribution layer, a transmission layer, and a wound contact layer. The overall height of the dressing can vary based on the layers selected for various embodiments, and the dressing compartment 110 can be sized accordingly. The dressing 114 can be configured to have a perimeter of a number of different shapes, and the perimeter of the dressing compartment 110 can be shaped accordingly to indicate the type of dressing included in the kit 100.

In operation, the wound dressing 114 is sealed over a wound site forming a wound cavity. The pump 122 provides a source of a negative pressure to the dressing 114. Fluid is drawn towards the orifice through the wound dressing from a wound site below the wound contact layer. The fluid moves towards the orifice through the transmission layer. As the fluid is drawn through the transmission layer, wound exudate is absorbed into the absorbent layer.

Some embodiments of the dressing 114 can have a port configured to receive an end of the conduit 116 (e.g., a first end of the conduit), though such port is not required. Accordingly, a port may be preattached to the dressing 114 in some embodiments and the conduit 116 can be provided separately. In some embodiments, the conduit 116 can otherwise pass through and/or under the dressing 114 to supply a source of reduced pressure to a space between the dressing 114 and the wound so as to maintain a desired level of reduced pressure in such space.

The components of the reduced pressure wound therapy systems can be manufactured in a wide variety of different models or versions, wherein the size of the dressing 100 can be varied to accommodate a wide range of wound sizes. For example, reduced pressure wound therapy systems can be made having the following sizes of dressing 114.

| Approximate Dressing Size |
| --- |
| 10 cm × 20 cm |
| 10 cm × 30 cm |
| 10 cm × 40 cm |
| 15 cm × 15 cm |
| 15 cm × 20 cm |
| 15 cm × 30 cm |
| 20 cm × 20 cm |
| 25 cm × 25 cm |

The desired shape and size of the wound dressing 114 can be selected based on the size and type of wound for which it will be used. The general shape of the wound dressing can be square, ovular, rectangular, lobed, winged, bridged, or otherwise. The dressing can have rounded corner regions. It will be appreciated that wound dressings according to other embodiments of the present invention can be shaped differently such as square, circular or elliptical dressings, or the like. Accordingly, the length, width, and shape of the dressing compartment can be variably sized to match and/or fit a particular shape and size of a dressing contained therein. The height of the dressing compartment can be variably sized, in some embodiments, based at least partly on a number of dressings to include in the packaging, for example one dressing, two dressings, or more.

In some embodiments, it may be preferable for the wound site to be filled partially or completely with a wound packing material. This wound packing material is optional, but may be desirable in certain wounds, for example deeper wounds. The wound packing material can be used in addition to the wound dressing 114. Further, some embodiments may further comprise one or more separate adhesive strips or sealing strips configured to seal the wound dressing 114 to skin surrounding a wound. Some kits may additionally include preparation materials including tools or compounds for preparing a wound site for treatment. Accordingly, some embodiments of the reduced pressure wound therapy kit 100 may include additional detachable compartments or additional storage in the dressing compartment 110 for other system components such as wound packing materials, sealing strips, preparation materials, and the like.

Pump compartment 120 can include a recessed portion 122 for storage of pump 124. As illustrated in FIG. 1, in one non-limiting example the pump compartment 120 may have an upper panel comprising one or more recessed portions, a bottom panel, and three side walls extending between the upper and bottom panels. Other embodiments described herein may include four side walls. After removal of the pump 124 for therapy, a clinician or user can detach the pump compartment 120 from the dressing compartment 110, for example by tearing along perforation line 130. Accordingly, the pump compartment 120 can be discarded after removal of its contents while the dressing compartment 110 can be retained to store any unused dressings 116 and for the instructions 112. In some embodiments, either or both of the pump compartment 120 and the dressing compartment 110 can be constructed from biodegradable/biocompostable materials, and are thus environmentally friendly.

In some embodiments, as in the illustrated embodiment, the pump 124 can be of a sufficiently small and portable size to be supported on a user's body or in a user's clothing. For example, the pump 124 can be sized to be attached using adhesive medical tape or otherwise to a person's skin in a comfortable location, adjacent to or on the dressing 114 or otherwise. Further, the pump 124 can be sized to fit within a person's pants or shirt pocket, or can be tethered to a person's body using a lanyard, pouch, or other suitable device or article.

In some embodiments, the pump 124 can be powered by one or more batteries (for example, two batteries) and can weigh approximately 84 grams, including the weight of the batteries. In some embodiments, the kit can include batteries for the pump 124.

In some embodiments, an upper panel of the pump compartment 120 can include a number of recesses in order to provide a medical device kit in which more than one part is provided for user assembly of the pump. For example, a three-part pump system can be provided in three separate blister packs such as a negative pressure pump pack, a separate battery pack, and an optional extension suction conduit pack. The exterior surface of the upper panel of the pump compartment 120 adjacent to the recesses can be provided with numbering. The recesses can be numbered according to the order of use of the parts received by the recesses. To illustrate, the negative pressure pump pack, separate battery pack, and optional extension suction conduit pack can be positioned in separate recesses (i.e., cut outs in the upper panel of the pump compartment 120) from left to right across the pump compartment 120 and can be numbered according to the order in which a user should remove the packs for assembling the pump. The instructions printed on the dressing compartment 110, or separately printed instructions on the pump compartment 120, can refer to the number of the component or pack and guide the user through the assembly process. Another example of a multiple recess pump compartment 120 can be used to provide a pump device where there is a negative pressure pump and a pump controller separate to the pump, and the user is required to assemble the pump and controller before use. Appropriate instructions and numbering can be provided for assembly on the exterior surface of the upper panel of one or both of the dressing compartment 110 and pump compartment 120. Sterile trays can be used to package the device assembly components instead of or in addition to blister packs in other embodiments.

Figure 2A:
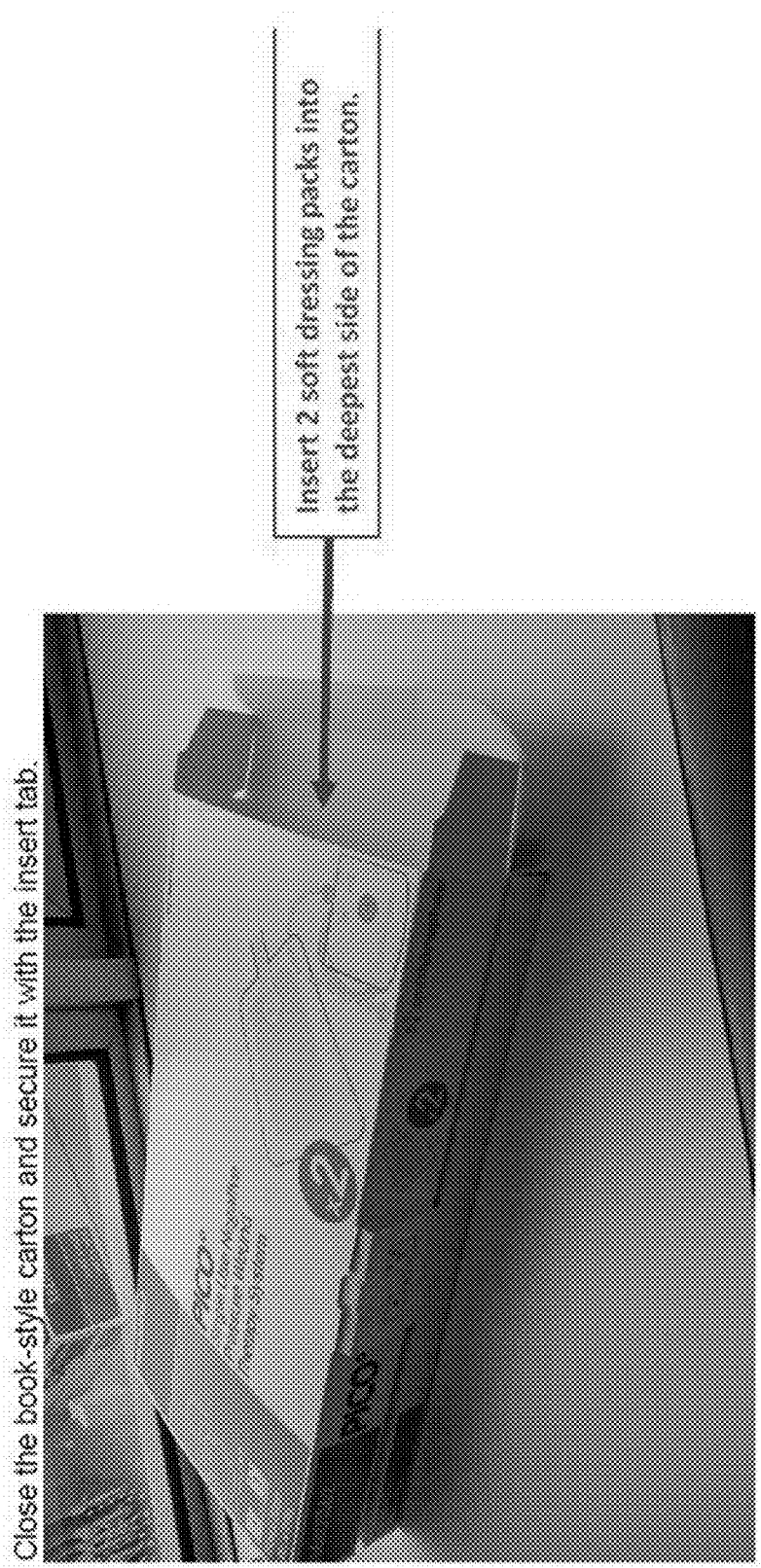
FIGS. 2A-2C illustrate an embodiment of a technique for assembling a reduced pressure wound therapy kit.
Figure 2B:
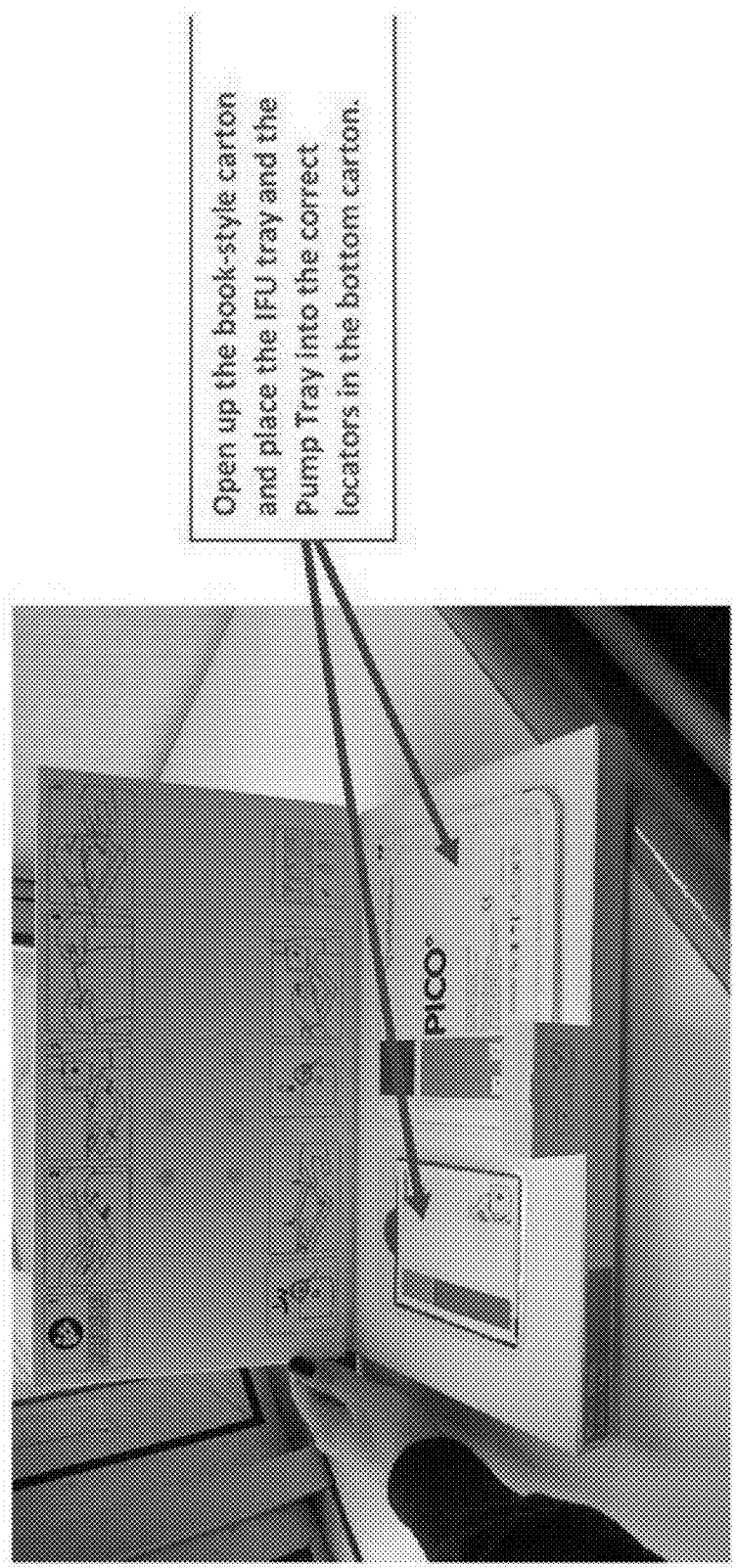
Figure 2C:
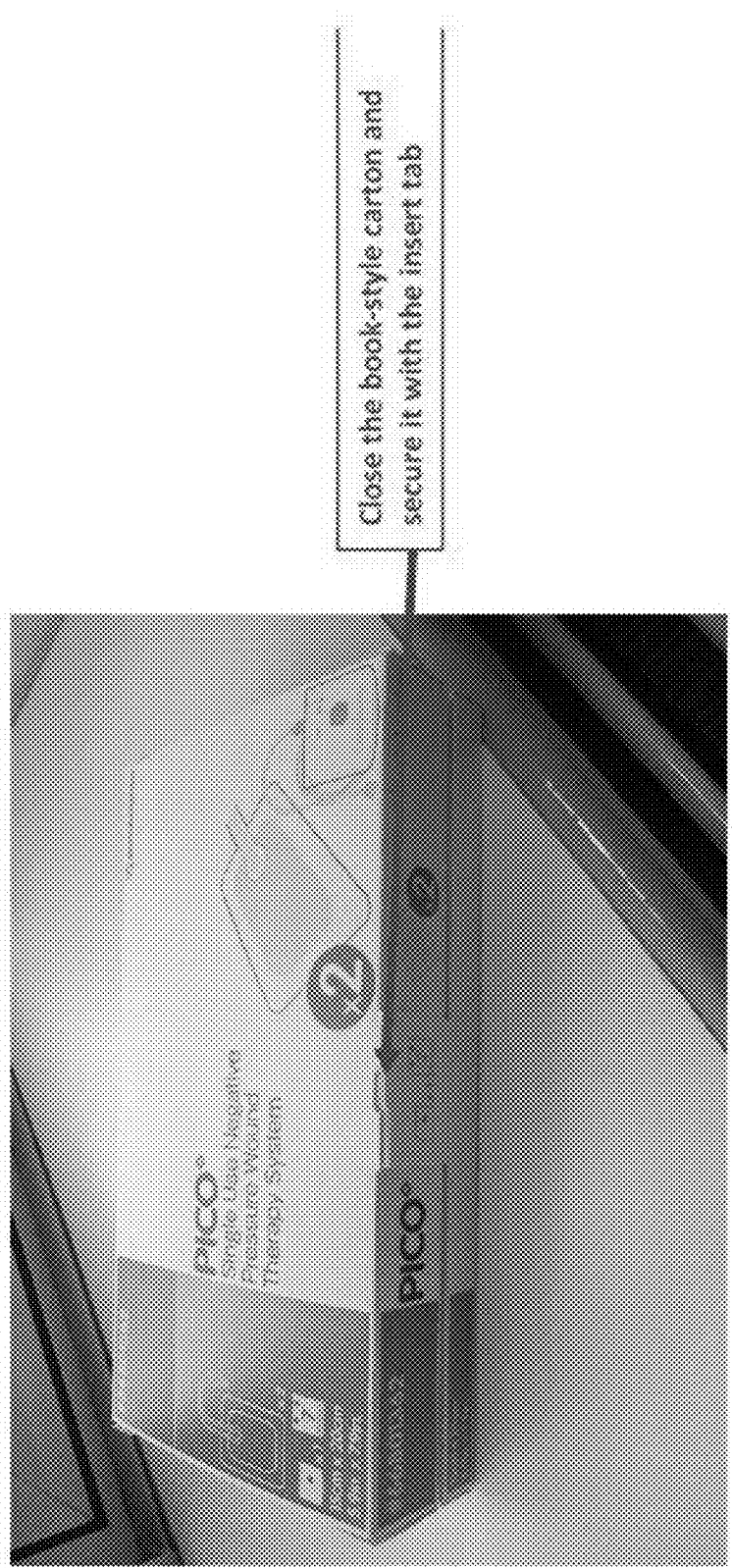

FIGS. 2A-2C illustrate an embodiment of a technique for assembling a reduced pressure wound therapy kit which utilizes packaging similar to but not the same as the embodiment of FIG. 1. FIG. 2A illustrates how dressings, for example sterile sealed dressings with or without pre-attached suction adapters, can be end-loaded into the dressing compartment. FIG. 2B illustrates how the book-style carton packaging can be opened so that an instruction manual packaging tray (IFU tray) and a pump packaging tray can be inserted into the correct recesses in the pump compartment. FIG. 2C illustrates how the packaging, now containing the contents of a reduced pressure wound therapy kit, can be affixed in the closed position using an insert tab connecting the pump compartment and the dressing compartment.

Figure 3A:
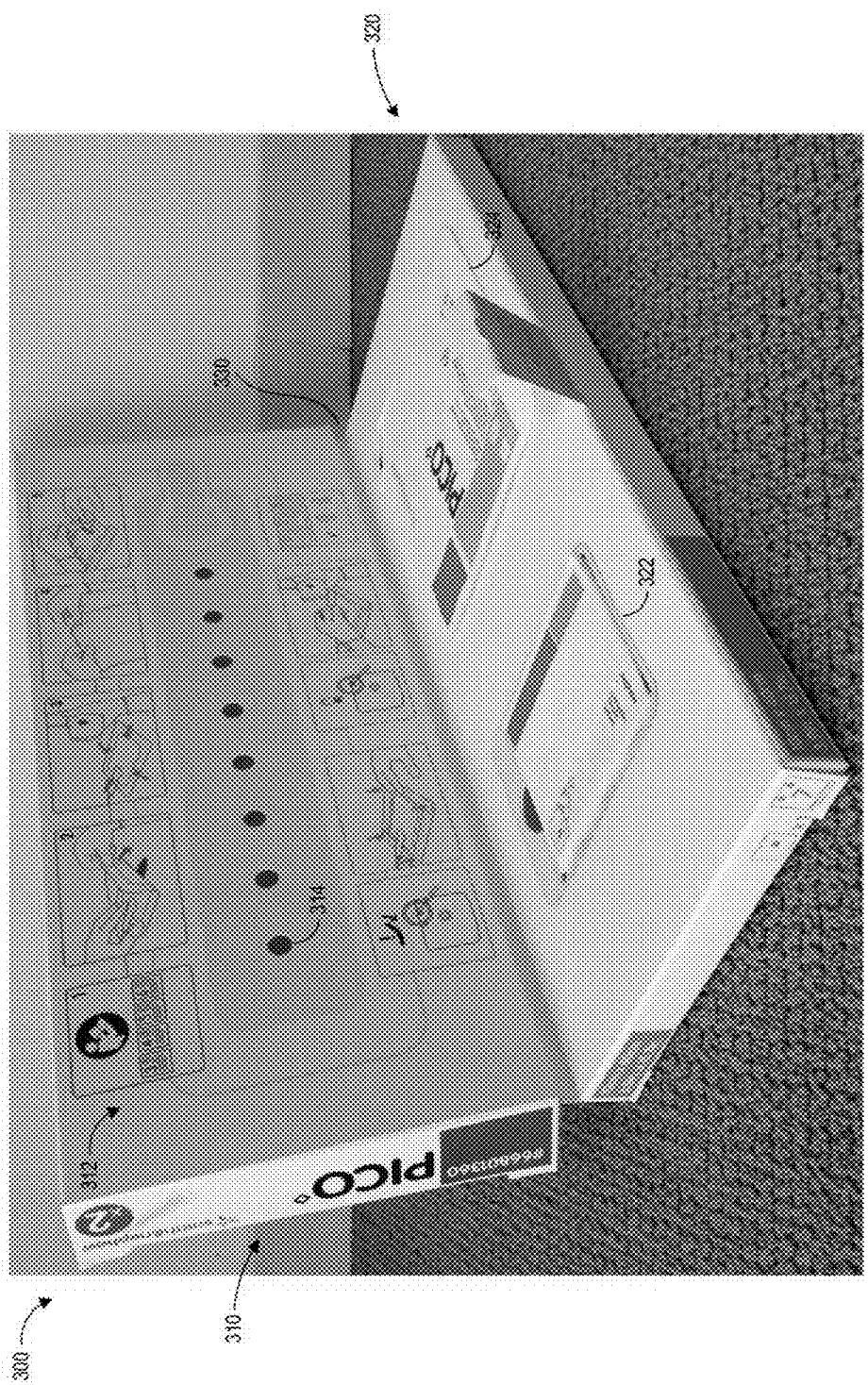
FIGS. 3A-3B illustrate an embodiment of a reduced pressure wound therapy kit including a sterile tray.
Figure 3B:
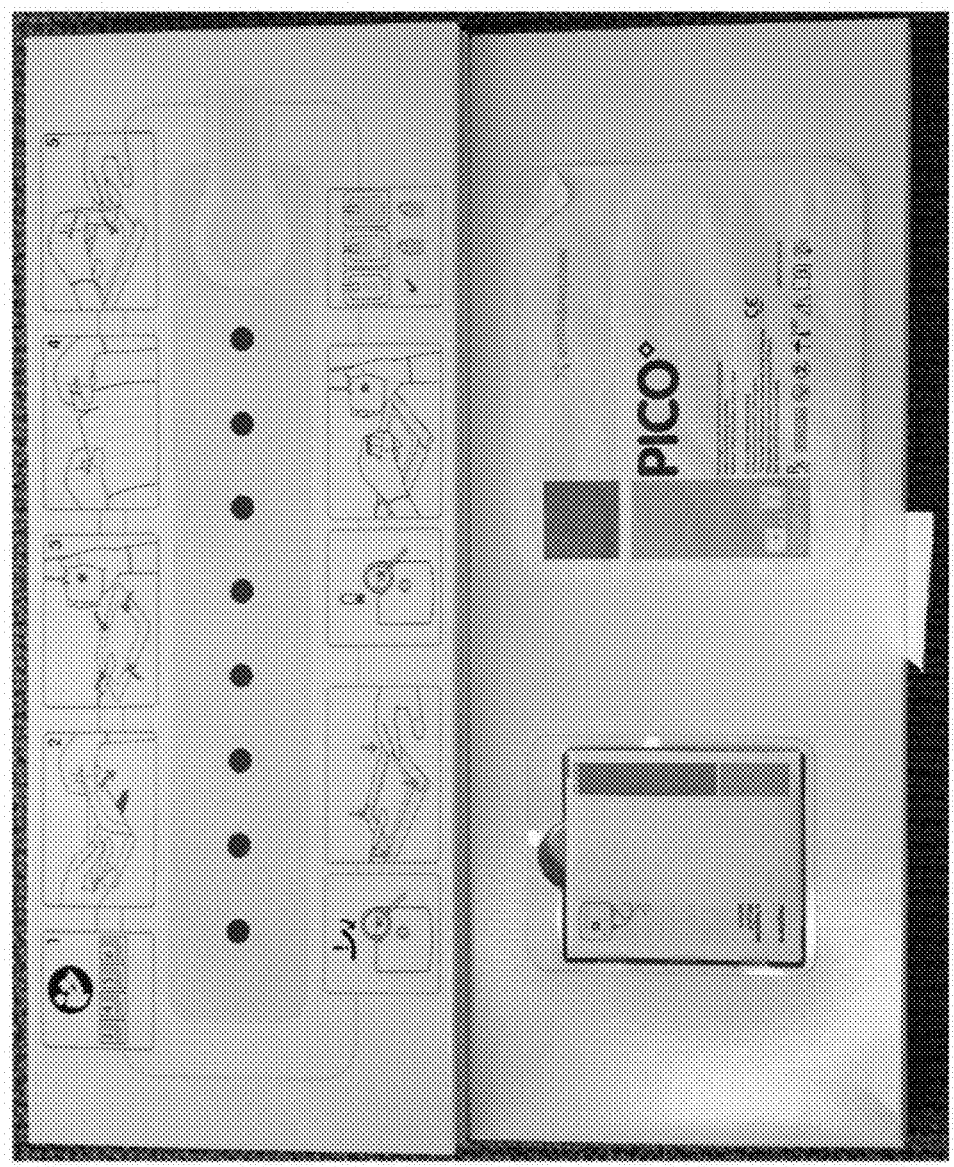

FIGS. 3A-3B illustrate an embodiment of a reduced pressure wound therapy kit 300 including a sterile pump packaging tray 324 and an instruction booklet packaging tray 322 inserted into corresponding recesses in the pump compartment 320. The pump compartment 320 of the packaging 300 can have one or more recesses (shown at 422 and 424, respectively, in FIG. 4H) configured to receive and support the sterile pump packaging tray 324 and a tray 322 containing instructions for use of the pump. These recesses may be provided on an inward-facing surface (which may be an upper panel) of the pump compartment 320.

The pump compartment 320 and the dressing compartment 310 can be folded open along hinge 330 to reveal the sterile pump packaging tray 324 and instruction booklet packaging tray 322 of the pump compartment 320 as well as the instructions 312 and dressing viewports 314 of the dressing compartment 310. In some embodiments, hinge 330 may include a number of perforations or weakened lines such that a clinician or user can easily separate the dressing compartment 310 and the pump compartment 320 after removing the contents of the pump compartment 320, retaining dressing compartment 310 and any unused dressings stored therein.

Dressing compartment 310 optionally includes a number of viewports 314 configured as through holes through the inward-facing surface (which may be an upper panel) of the dressing compartment 310. Although one particular number and arrangement of viewports 314 is depicted in FIGS. 3A-3B, others are possible. As described in International Patent Application No. PCT/IB2013/002060, a masking or obscuring layer of a dressing can have a particular number and arrangement of viewing windows arranged across at least a portion of the area of the masking layer, for example as circular through holes. In some embodiments, the viewports 314 can be arranged in a matching configuration with the viewing windows in the masking layer. In other embodiments, the viewports 314 can be arranged in a different configuration from the viewing windows in the masking layer. In still other embodiments, the dressings contained in the dressing compartment 310 may not have a masking layer or may not have viewing windows in a masking layer, and dressing compartment 310 can still have viewports 314.

As illustrated in FIGS. 3A-3B, the inward-facing surface of the dressing compartment 310 may include information such as instructions for applying and/or using the components of the system. For example, a series of images may be printed on the inward-facing surface of the dressing compartment 310 to illustrate pictorially to a user how a wound dressing is to be applied and how a pump is to be used. The inward-facing surface may also include an image printed thereon of the wound dressing itself. Furthermore, the inward-facing surface may include images explaining to a user when the wound dressing may not be properly sealed to a patient's skin, when a battery of the pump is expiring, and/or when a dressing has become overly saturated with wound exudate. As illustrated in FIGS. 3A and 3B, in one embodiment an upper row of images may provide instructions to a user for applying and using the device. For example, box 1 instructs a user to read an instruction manual; box 2 instructs a user to apply the wound dressing over a wound; box 3 instructs a user to operate a pump, which may test the seal made by the dressing to skin surrounding the wound; box 4 instructs a user to tear off sealing strips used to further seal the wound dressing; and box 5 instructs a user to apply the sealing strips to the wound dressing. FIGS. 3A and 3B also illustrate a lower row of images, showing (from left to right), an image of an alarm on the pump indicating an inadequate seal; an image of sealing strips used to further seal a wound dressing to skin surrounding the wound; an image of low battery in the pump; an image showing a change of batteries; and an image illustrating saturation level of the wound dressing and when the wound dressing should be disposed.

Figure 4A:
FIGS. 4A-4O illustrate various views of packaging for the reduced pressure wound therapy kit of FIGS. 3A-3B in various configurations.
Figure 4B:
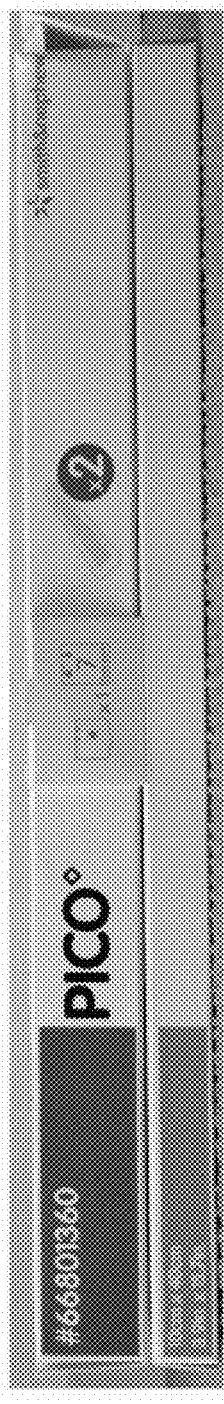
Figure 4C:
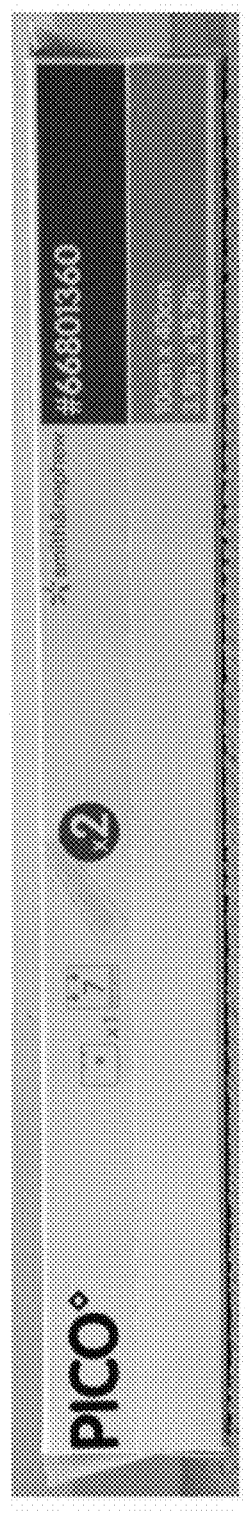
Figure 4D:
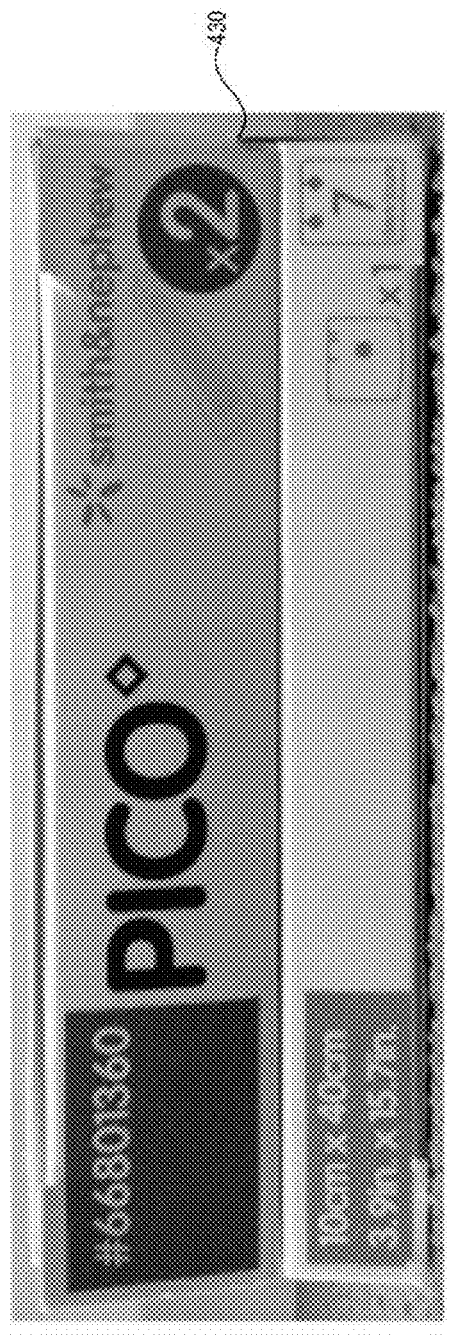
Figure 4E:
Figure 4F:
Figure 4G:
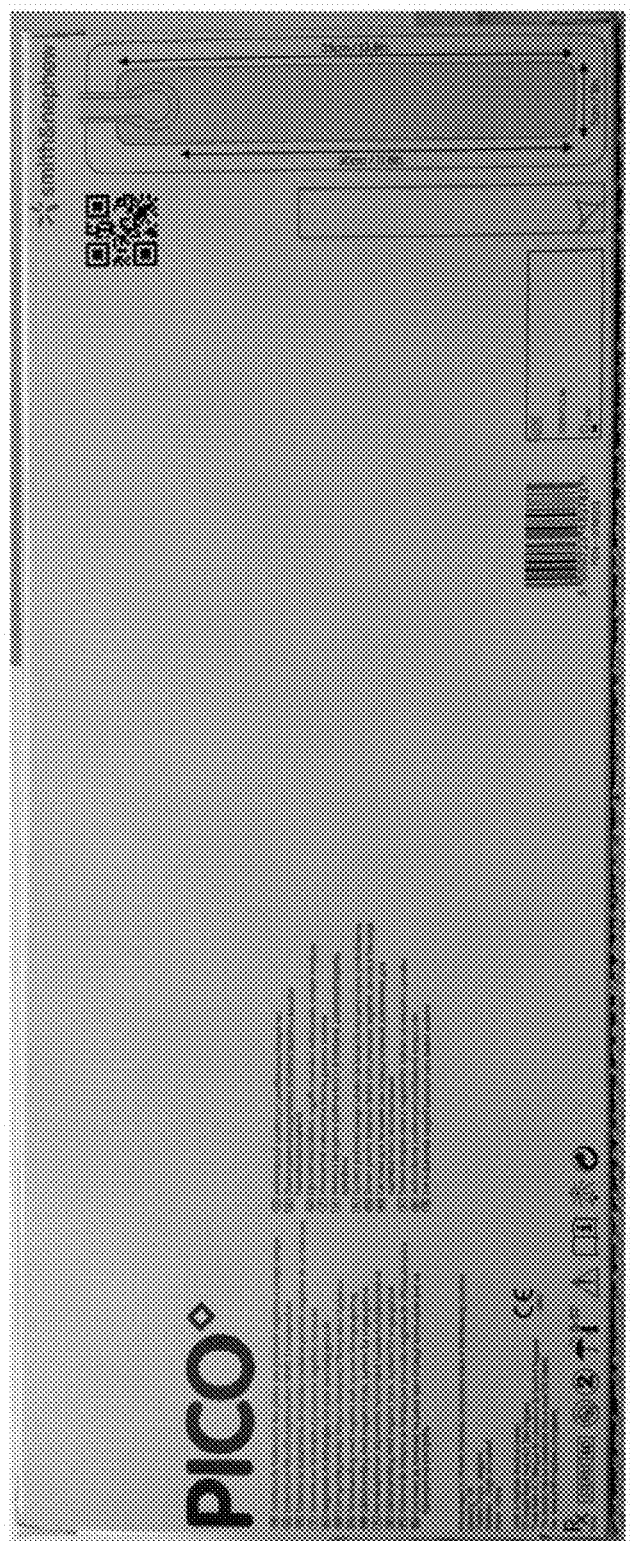

FIGS. 4A-4O illustrate various views of one embodiment of packaging 400 for the reduced pressure wound therapy kit of FIGS. 3A-3B in various configurations. FIG. 4A illustrates a perspective view of the packaging 400 in a closed configuration, showing the dressing compartment 410 and the pump compartment 420 closed and held together with a closure flap. FIG. 4B illustrates a front view of the packaging in the closed configuration. FIG. 4C illustrates a rear view of the packaging 400 in the closed configuration. FIG. 4D illustrates a left view of the packaging 400 in the closed configuration. FIG. 4E illustrates a right view of the packaging 400 in the closed configuration. FIG. 4F illustrates a top view of the packaging 400 in the closed configuration. FIG. 4G illustrates a bottom view of the packaging 400 in the closed configuration.

Figure 4H:
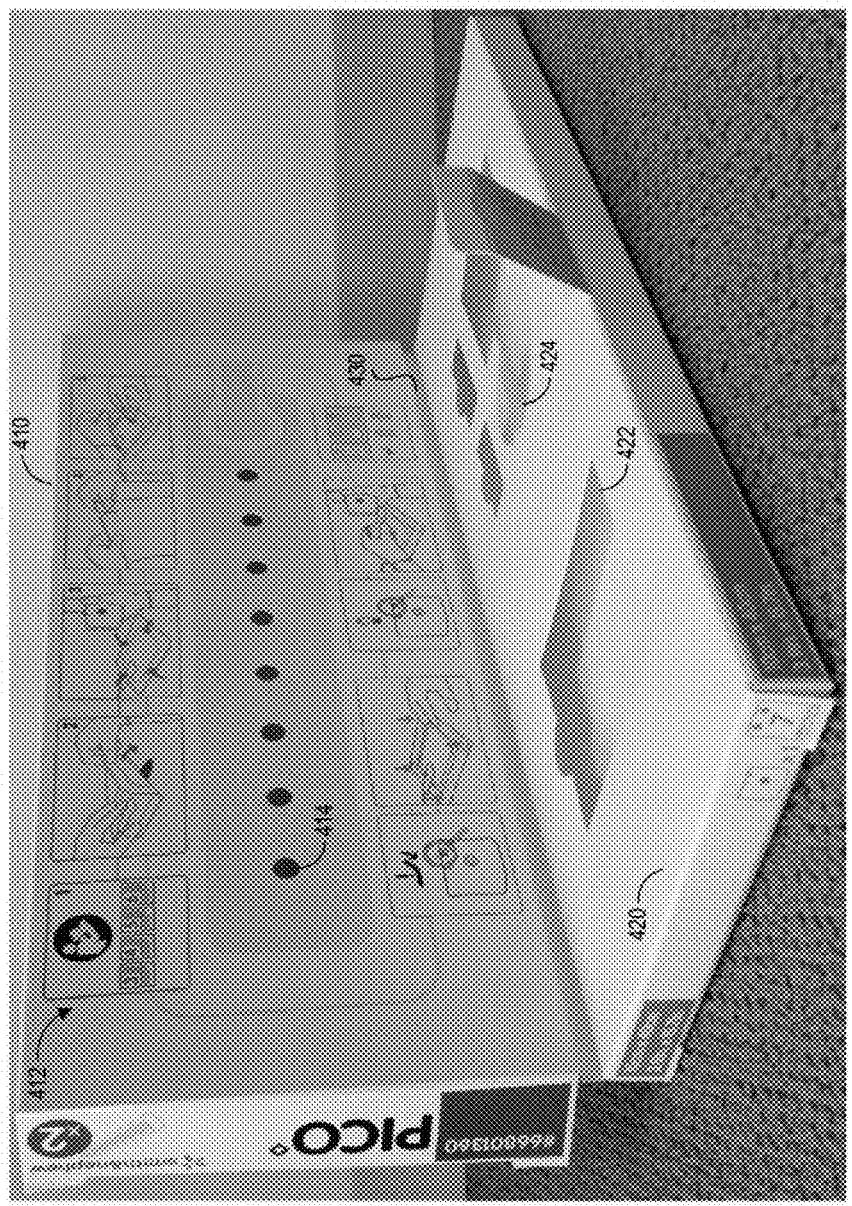
Figure 4I:
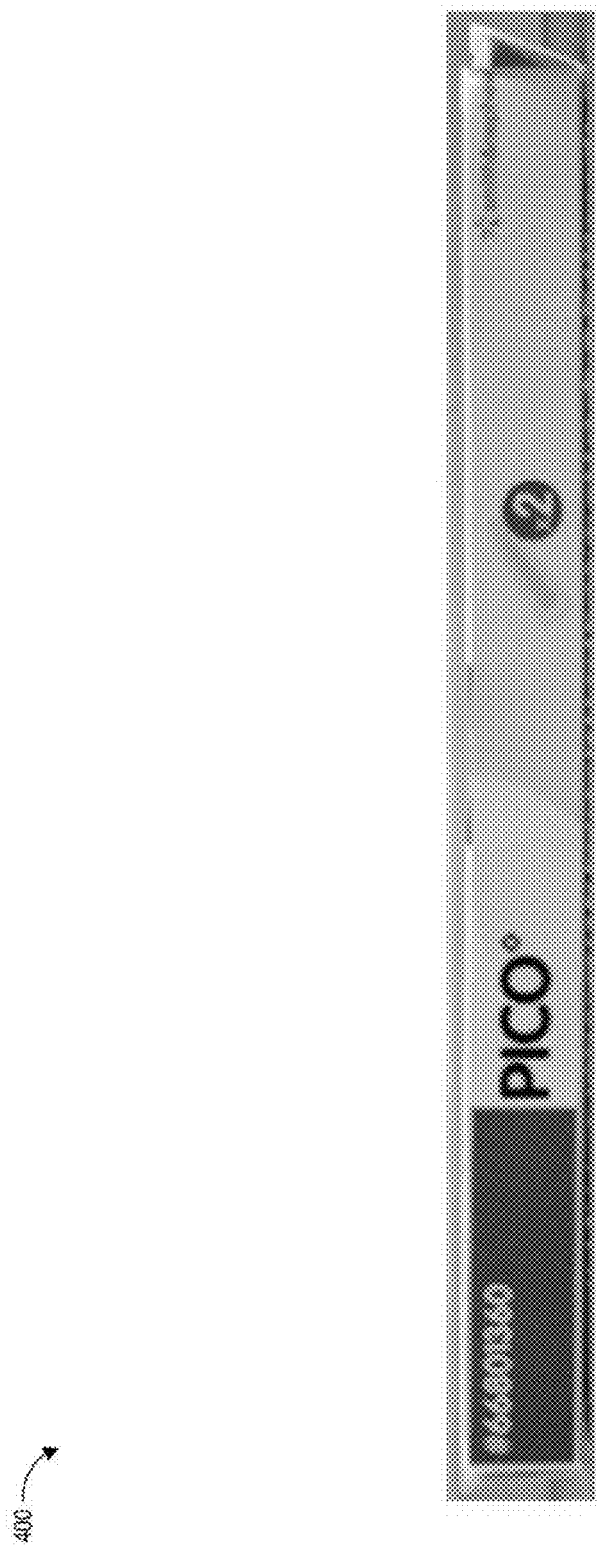
Figure 4J:
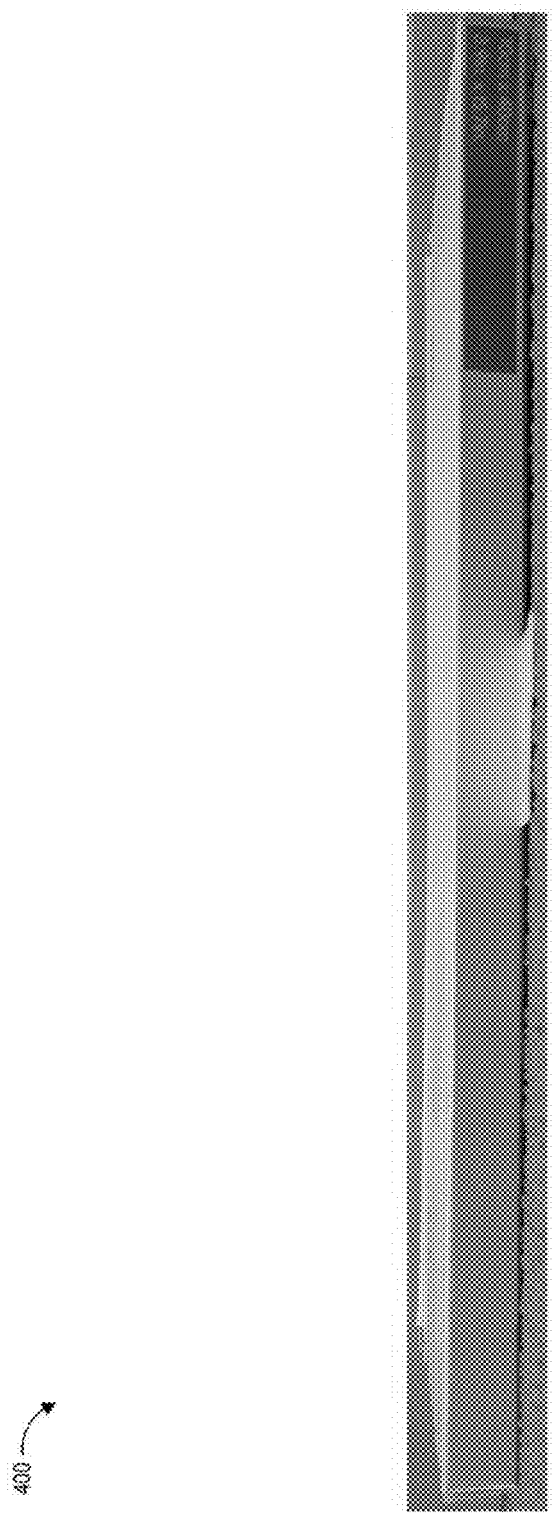
Figure 4K:
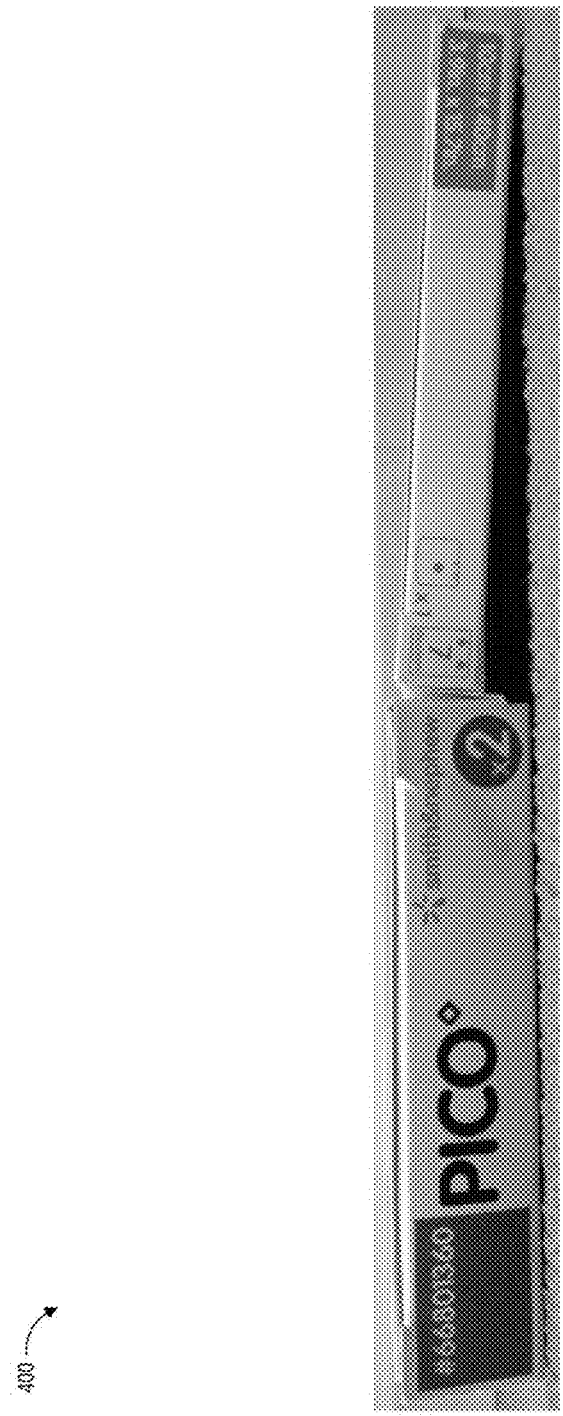
Figure 4L:
Figure 4M:
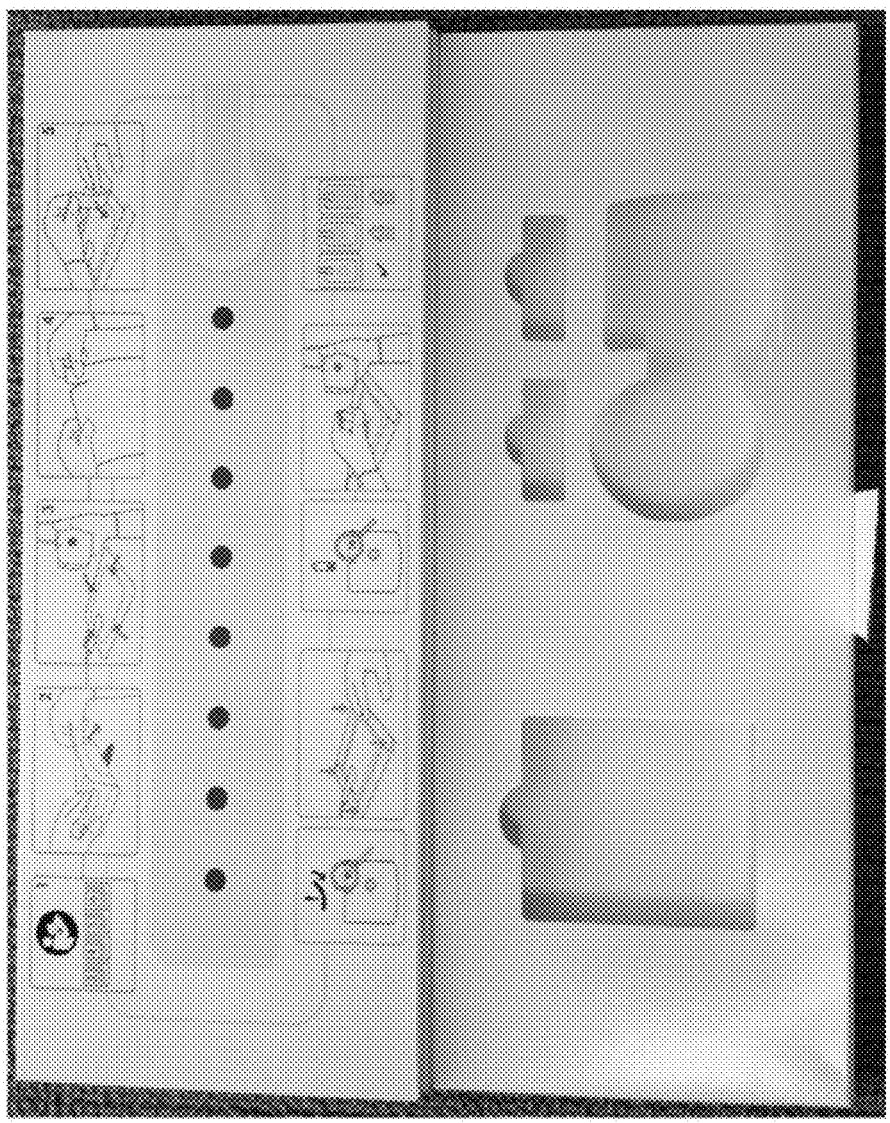
Figure 4N:
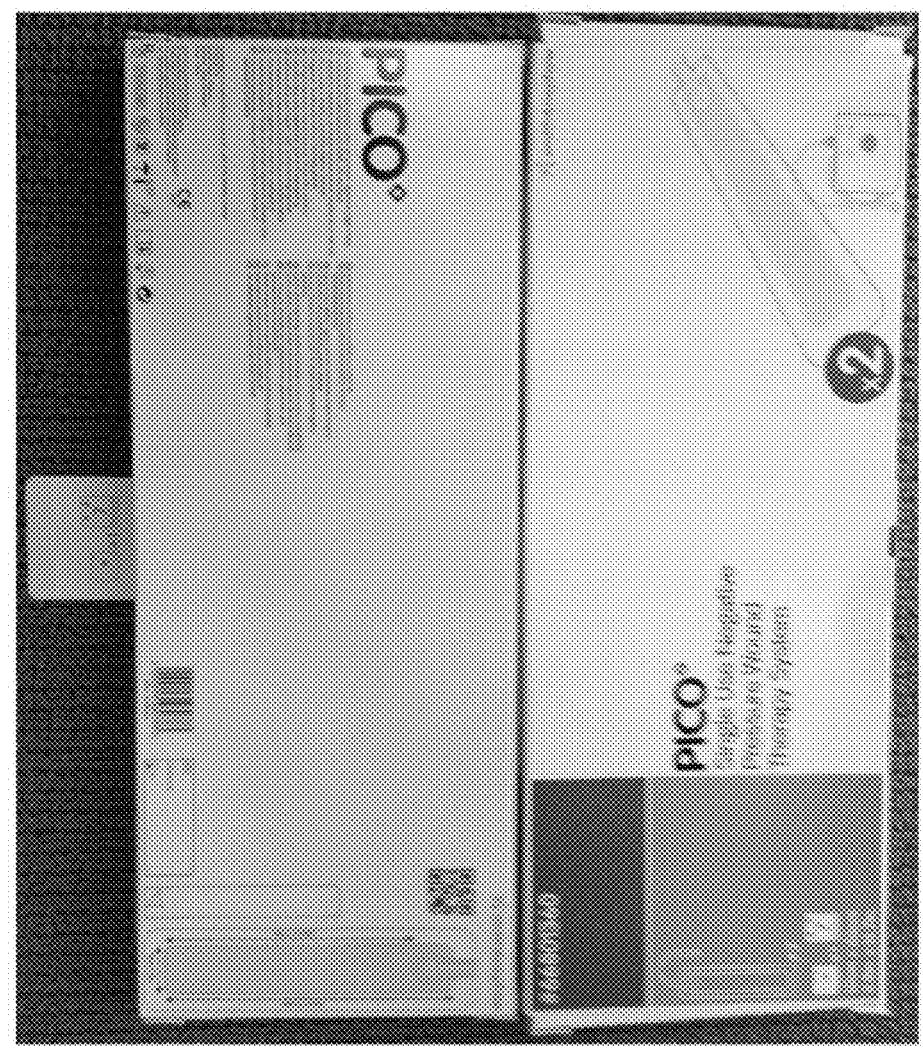
Figure 5A:
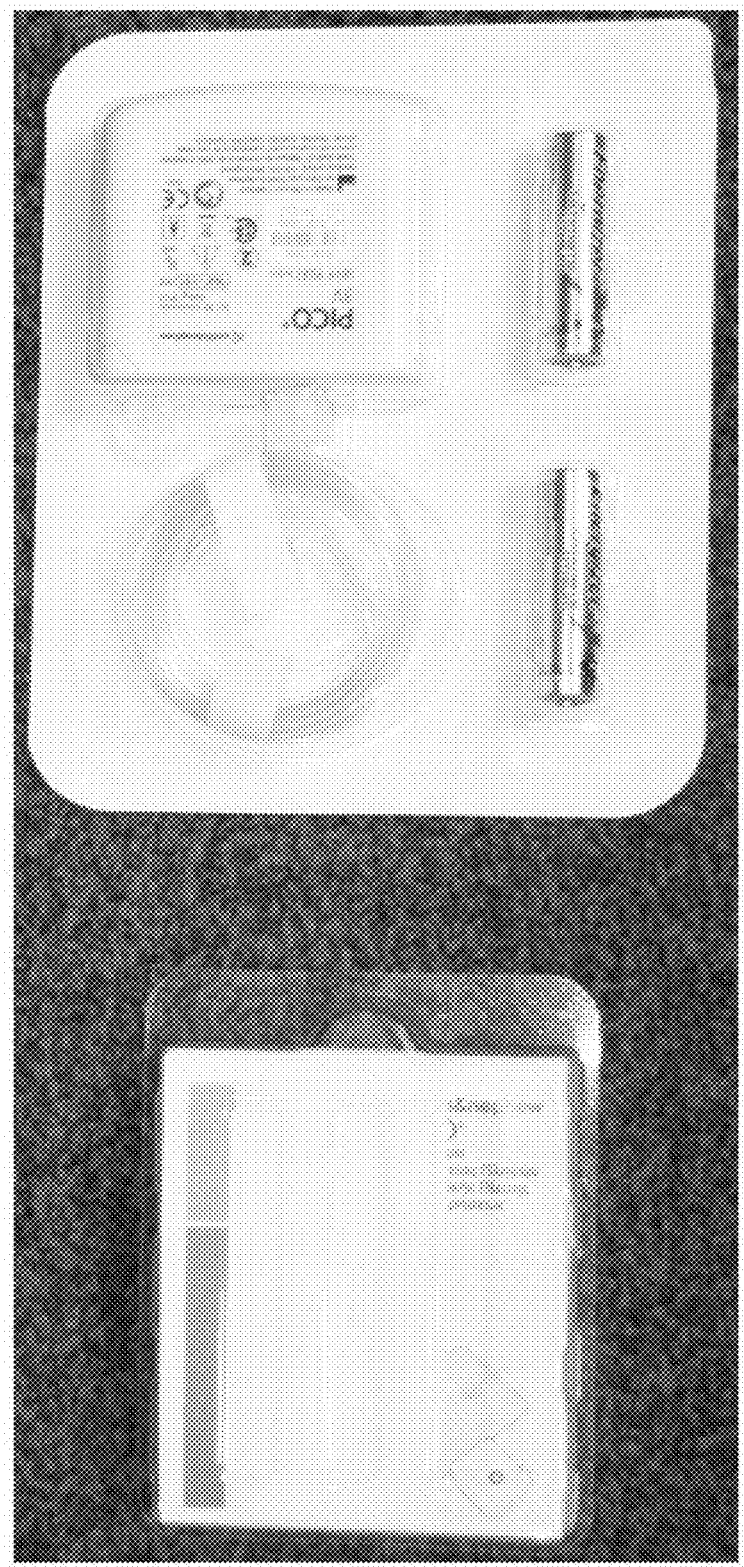
FIGS. 5A-5D illustrate various perspective views of trays for use with the packaging of FIGS. 4A-4O.
Figure 5B:
Figure 5C:
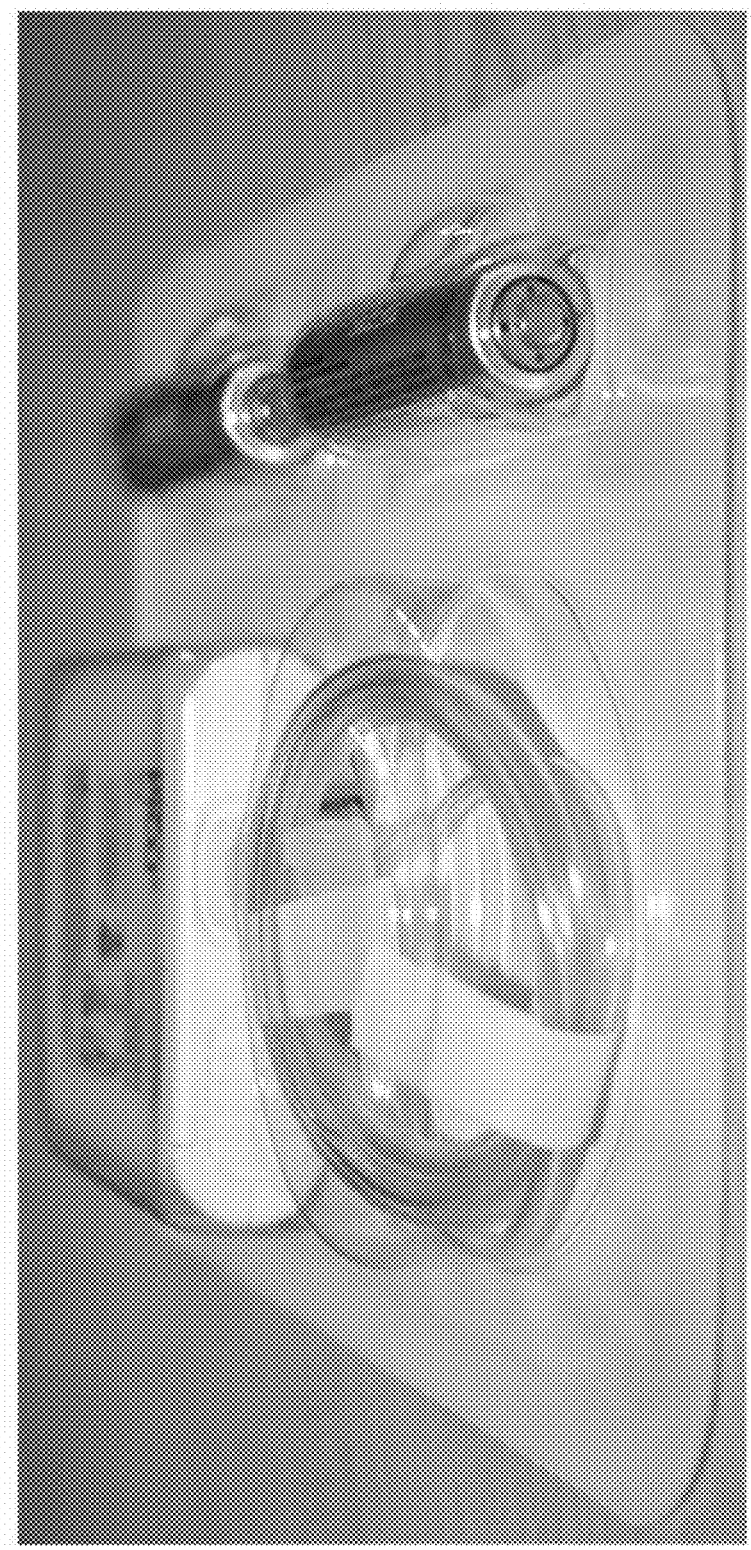
Figure 5D:

FIG. 4H illustrates a perspective view of the packaging 400 in a partially open configuration, showing the dressing compartment 410 and the pump compartment 420 folded open so that the instructions 412 and the viewing windows 414 on the dressing compartment 410 and the recesses 422, 424 on the pump compartment 420 are visible. FIG. 4I illustrates a front view of the packaging in a fully open configuration where the dressing compartment 410 and pump compartment 420 are folded apart so that the upper surface of the pump compartment 420 including recesses 422, 424 and the upper surface of the dressing compartment 410 including instructions 412 and viewing windows 414 are substantially parallel and are facing downward. FIG. 4I illustrates a front sidewall of the dressing compartment 410. FIG. 4J illustrates a rear view of the packaging 400 in the open configuration, displaying a front sidewall of the pump compartment 420. FIG. 4K illustrates a left view of the packaging 400 in the open configuration. FIG. 4L illustrates a right view of the packaging 400 in the open configuration. FIG. 4M illustrates a top view of the packaging 400 in the open configuration. FIG. 4N illustrates a bottom view of the packaging 400 in the open configuration.

FIG. 4O illustrates a view through the open end of the dressing compartment 410, showing the viewing windows 414 revealing a portion of the pump compartment 420.

FIGS. 5A-5D illustrate various perspective views of trays for use with the packaging of FIGS. 4A-4O. The instruction booklet tray has one recess configured to receive and support a booklet providing use instructions for the pump. The instruction booklet tray can have grooves or recesses sized and configured to facilitate a clinician's or user's access and removal of the instruction booklet.

The pump packaging tray can have one or more recesses configured to receive and support the components of the pump and other components. For example, the pump packaging tray can have a generally rectangular recess for receiving the pump, a number of smaller generally rectangular recesses for receiving batteries of the pump, and a generally circular recess for receiving the conduit and/or connector. Additionally, as illustrated, the pump packaging tray can have grooves or recesses sized and configured to facilitate a clinician's or user's access and removal of the various components of the pump therapy system. The pump packaging tray can be made from any suitable material that can be sterilized, including a recyclable virgin PETG Blue tinted 0.80 Eastman 6763 medical grade provided by Nelipak Custom Thermoformed Products. The pump packaging tray can be extruded from EASTAR Chemical Product EASTAR copolyester resin.

A cover can be sealingly positioned over the pump packaging tray to provide a bacteria and contaminant barrier to the contents of the pump packaging tray. For example, a sheet-like layer or film of TYVEK, paper, or any other suitable material can be sealed to a rim portion of the pump packaging tray. The cover can be made from any suitable material, including TYVEK, that is permeable to the sterilization gas but provides a barrier to bacteria and other contamination. The cover can be sealingly coupled with the pump packaging tray after all of the pump components are assembled therein. A rim portion can extend around the perimeter of the tray and can be adapted to rest against a portion of an exterior surface of the upper panel of the pump compartment surrounding an opening in the upper panel in order to support the pump packaging tray when placed in the opening.

Figure 6A:
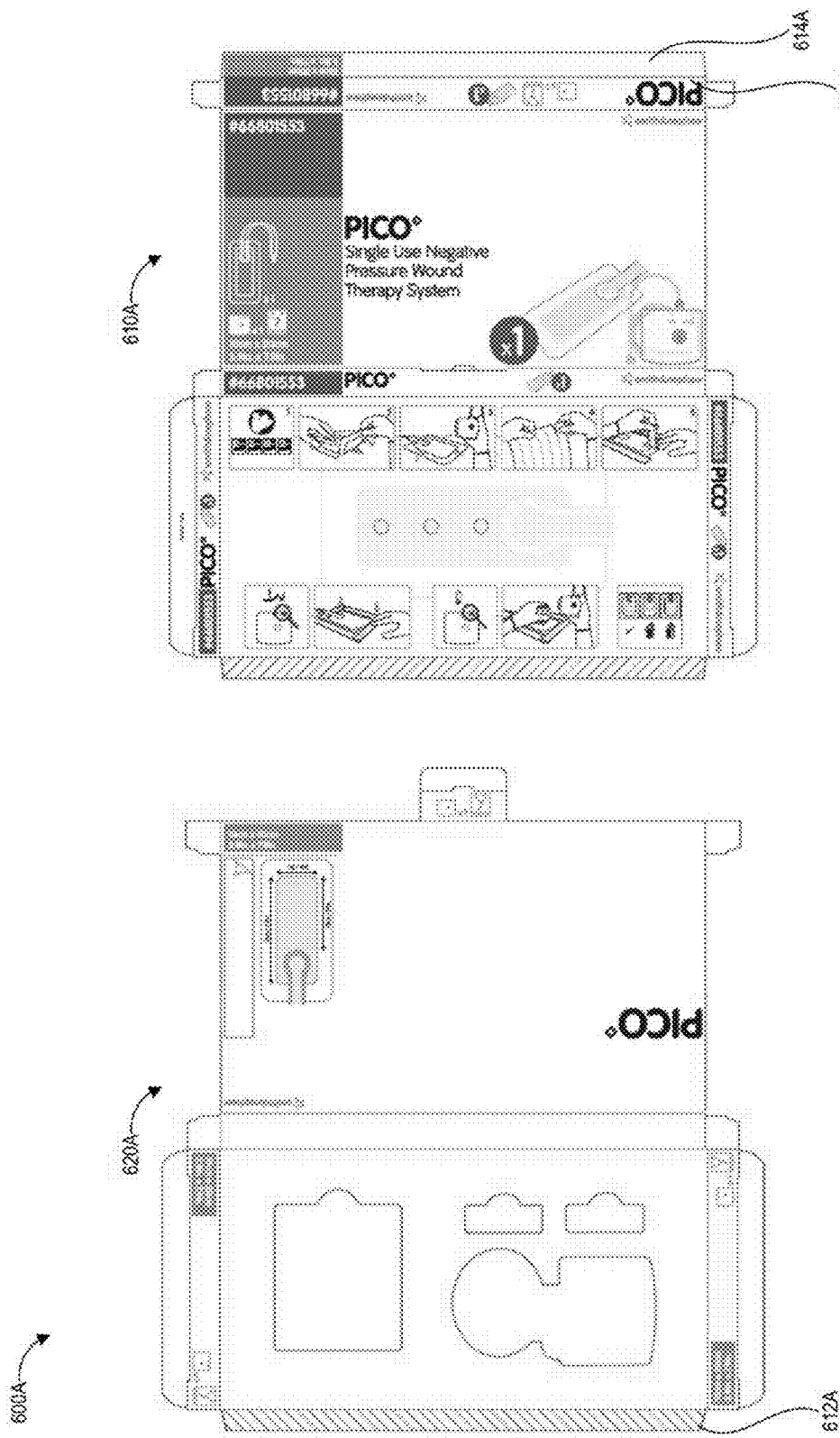
FIGS. 6A-6P illustrate two dimensional carton designs for various reduced pressure wound therapy kit packaging embodiments.
Figure 6B:
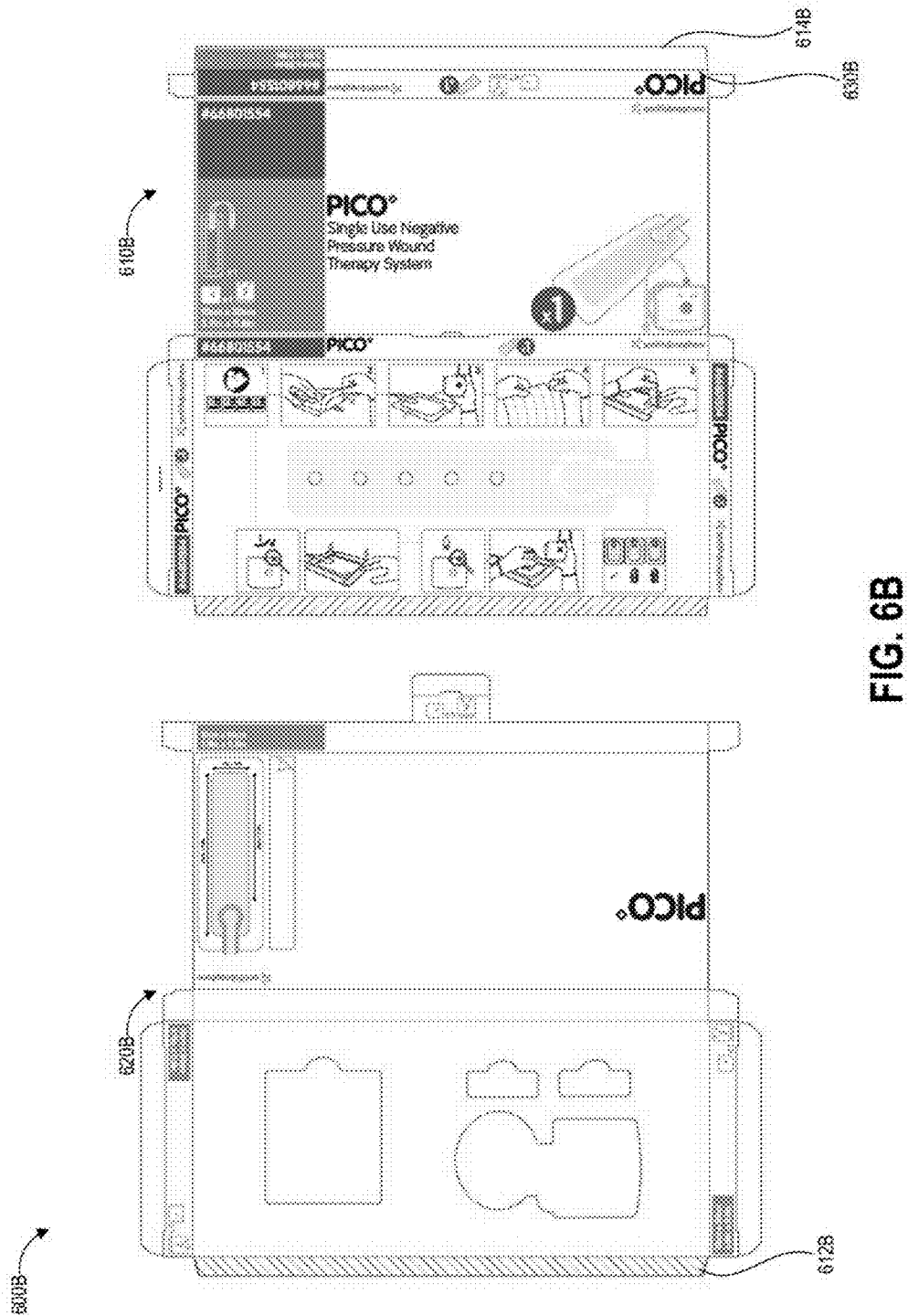
Figure 6C:
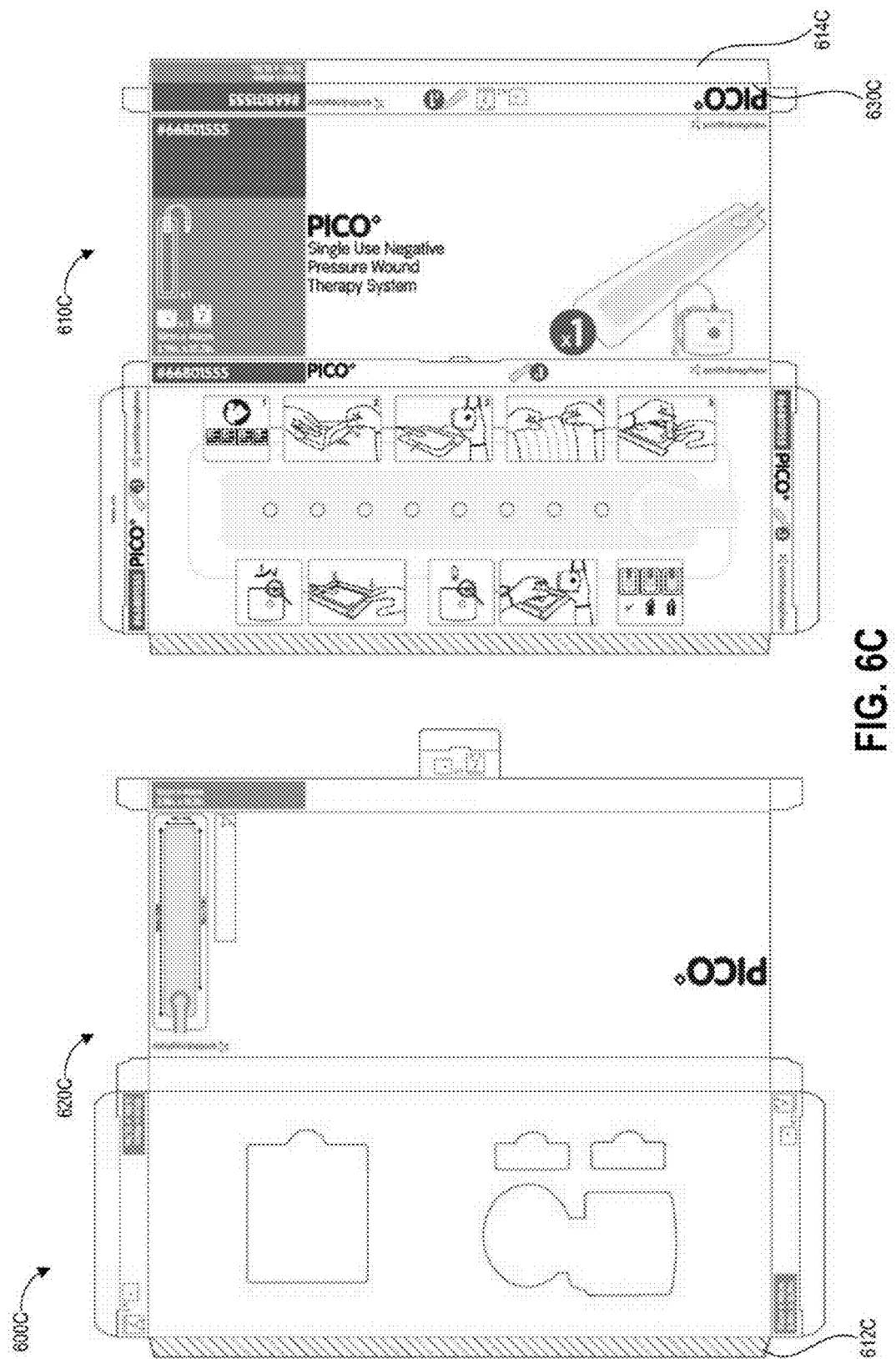
Figure 6D:
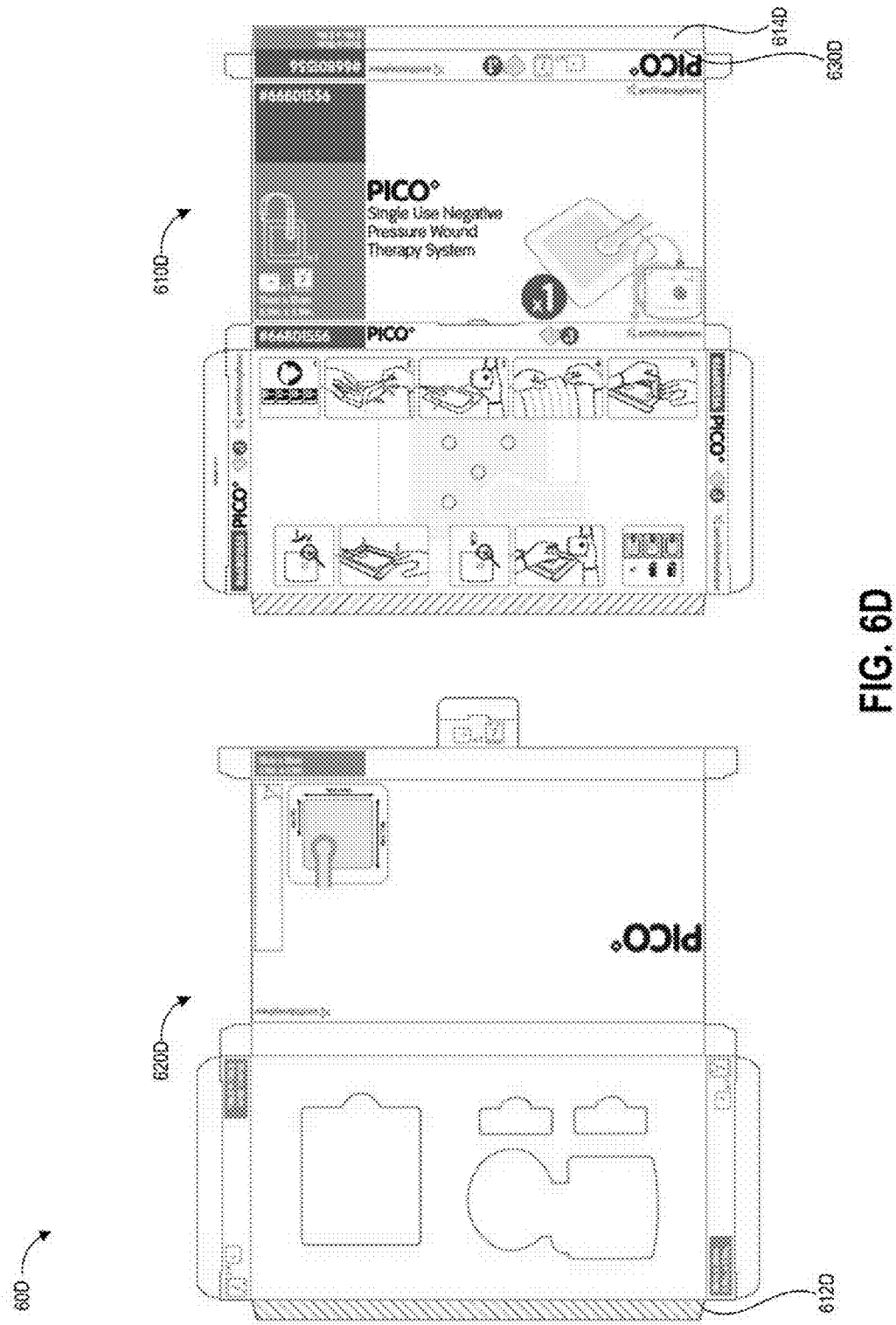
Figure 6E:
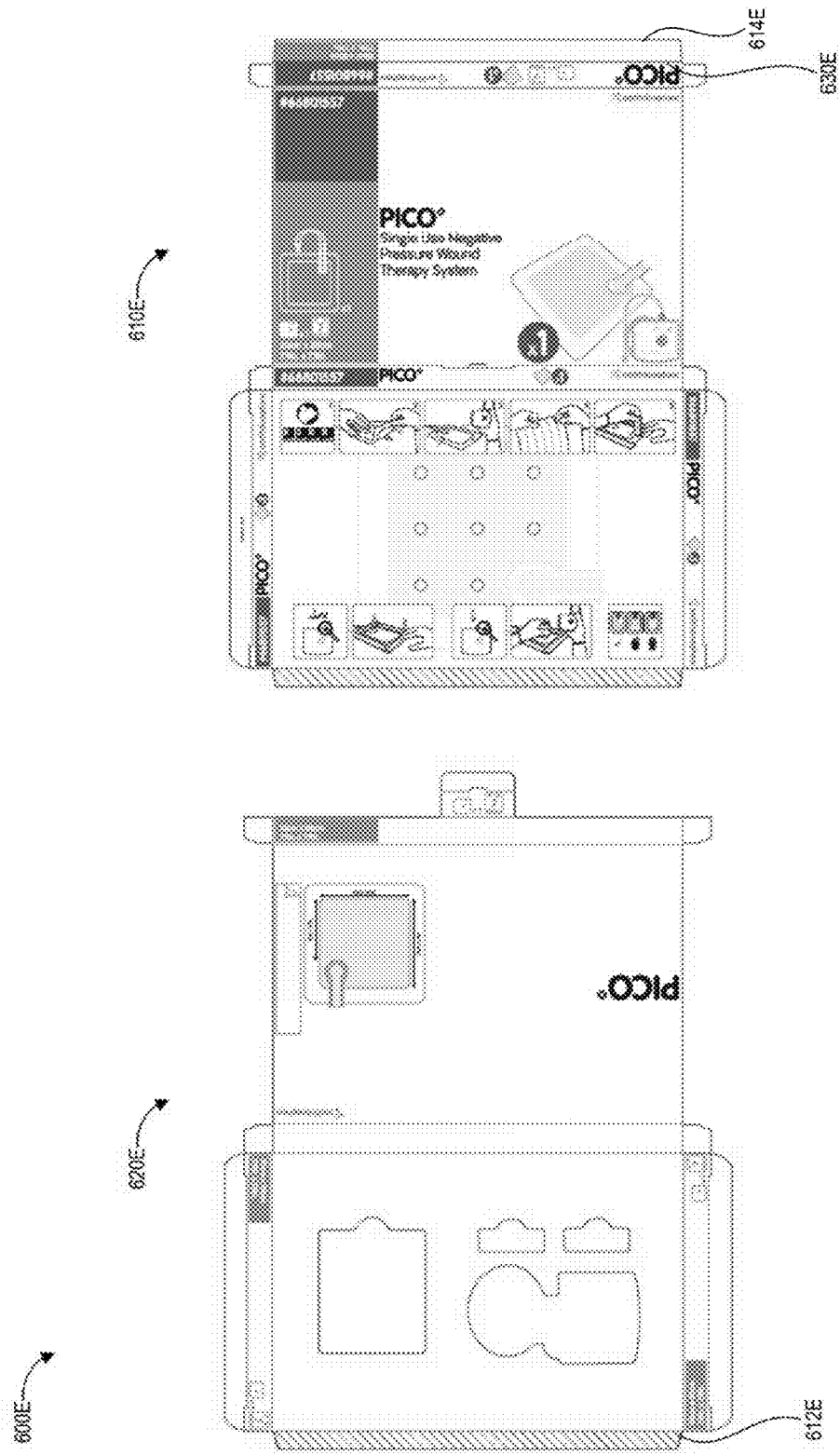
Figure 6F:
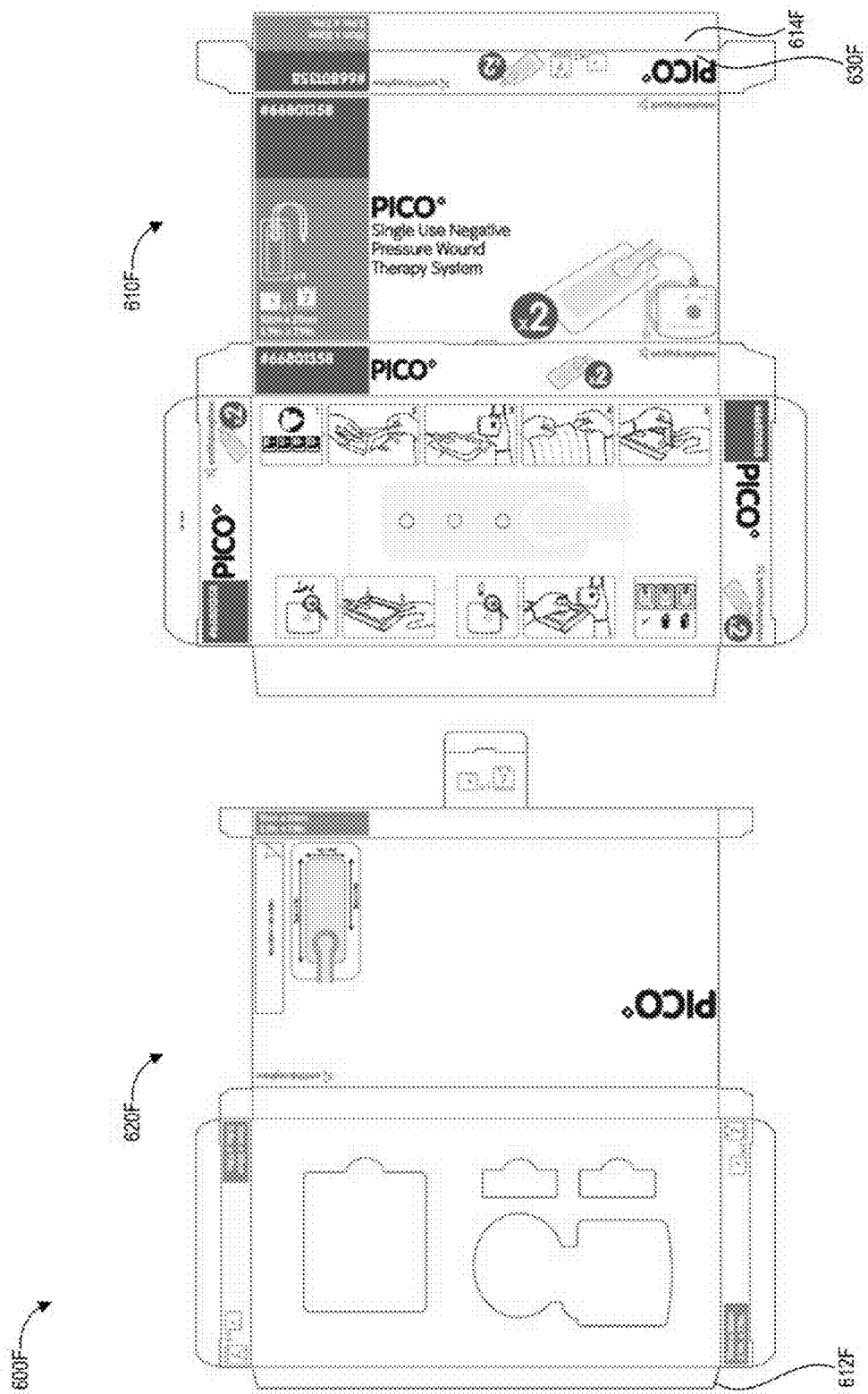
Figure 6G:
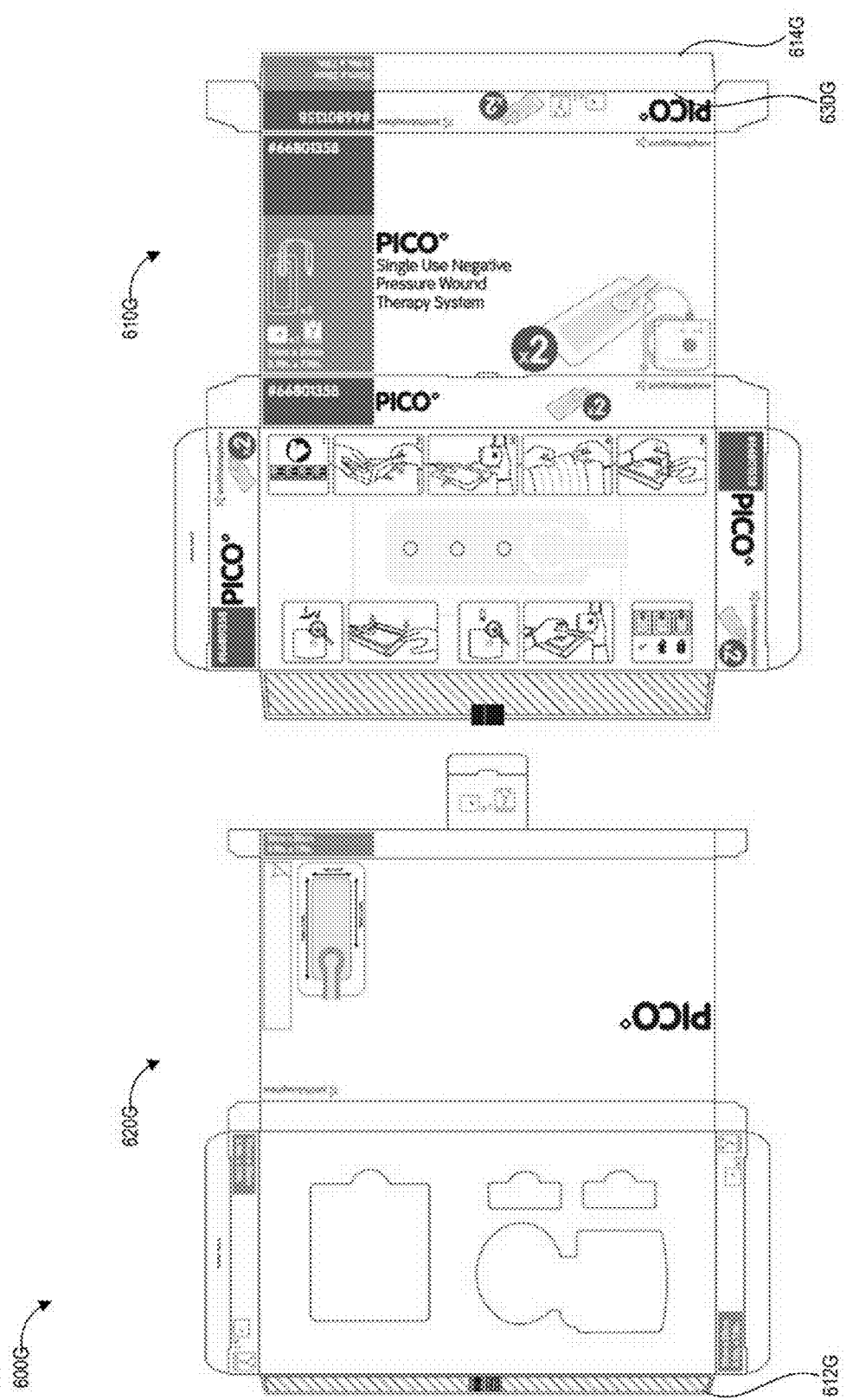
Figure 6H:
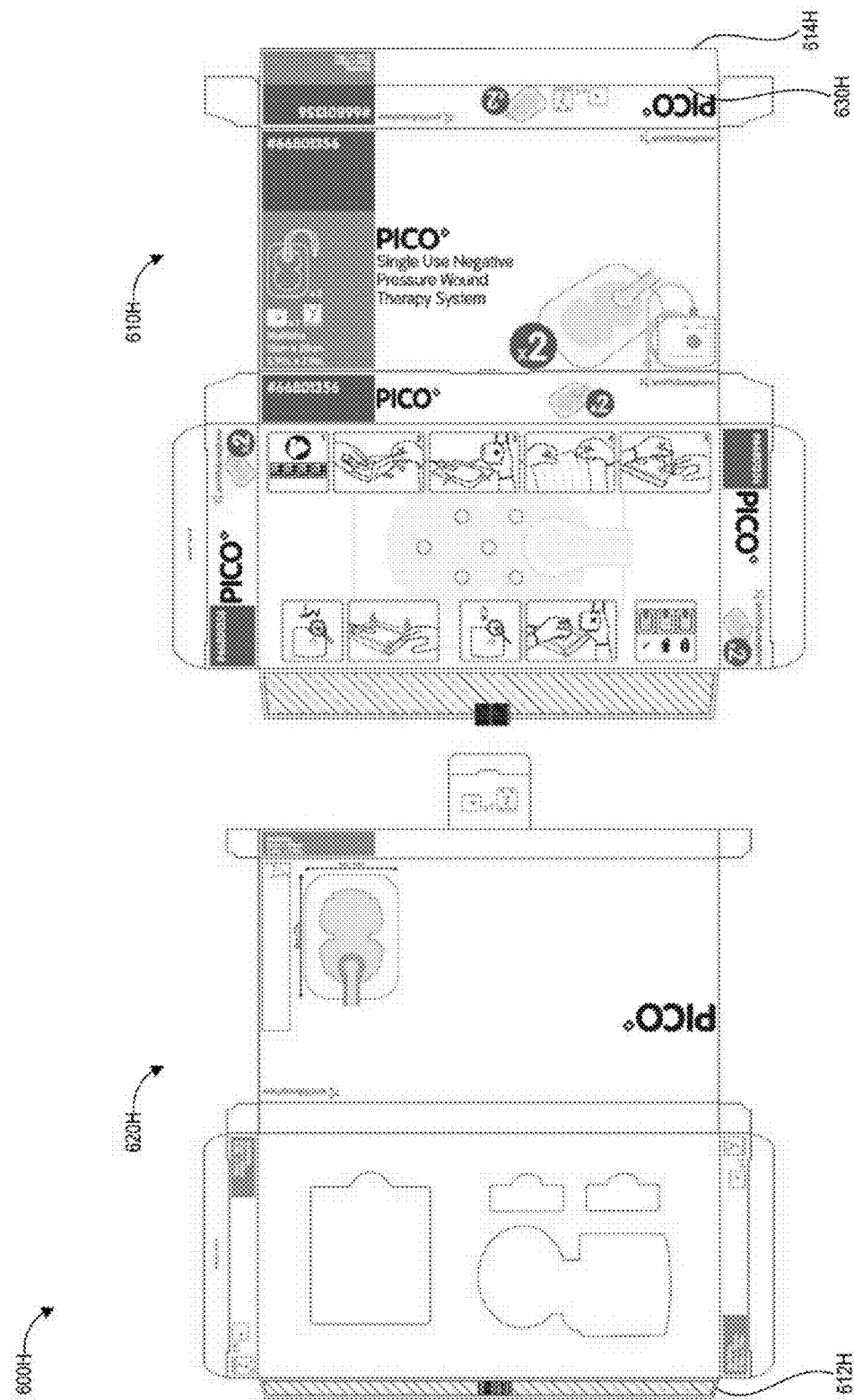
Figure 6I:
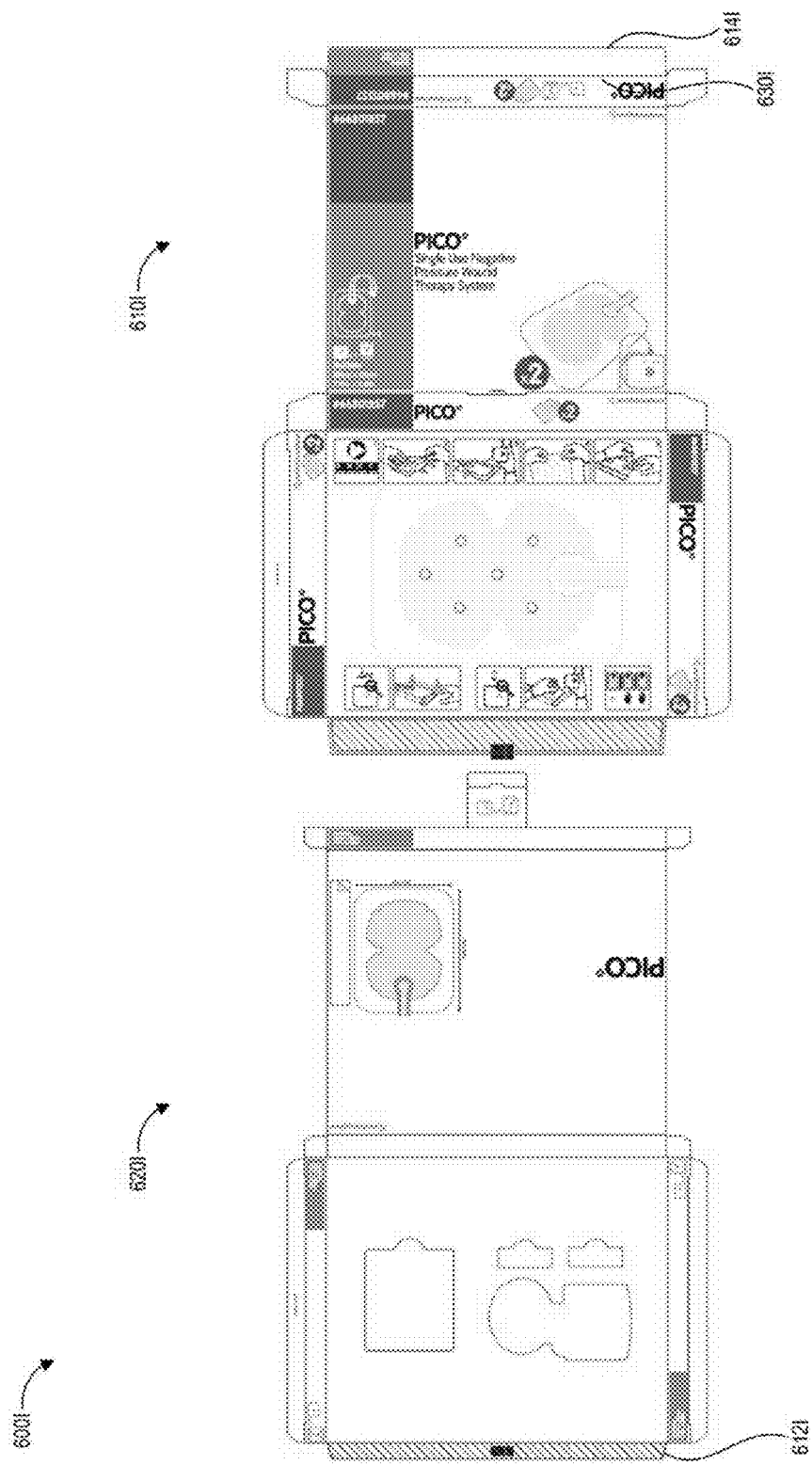
Figure 6J:
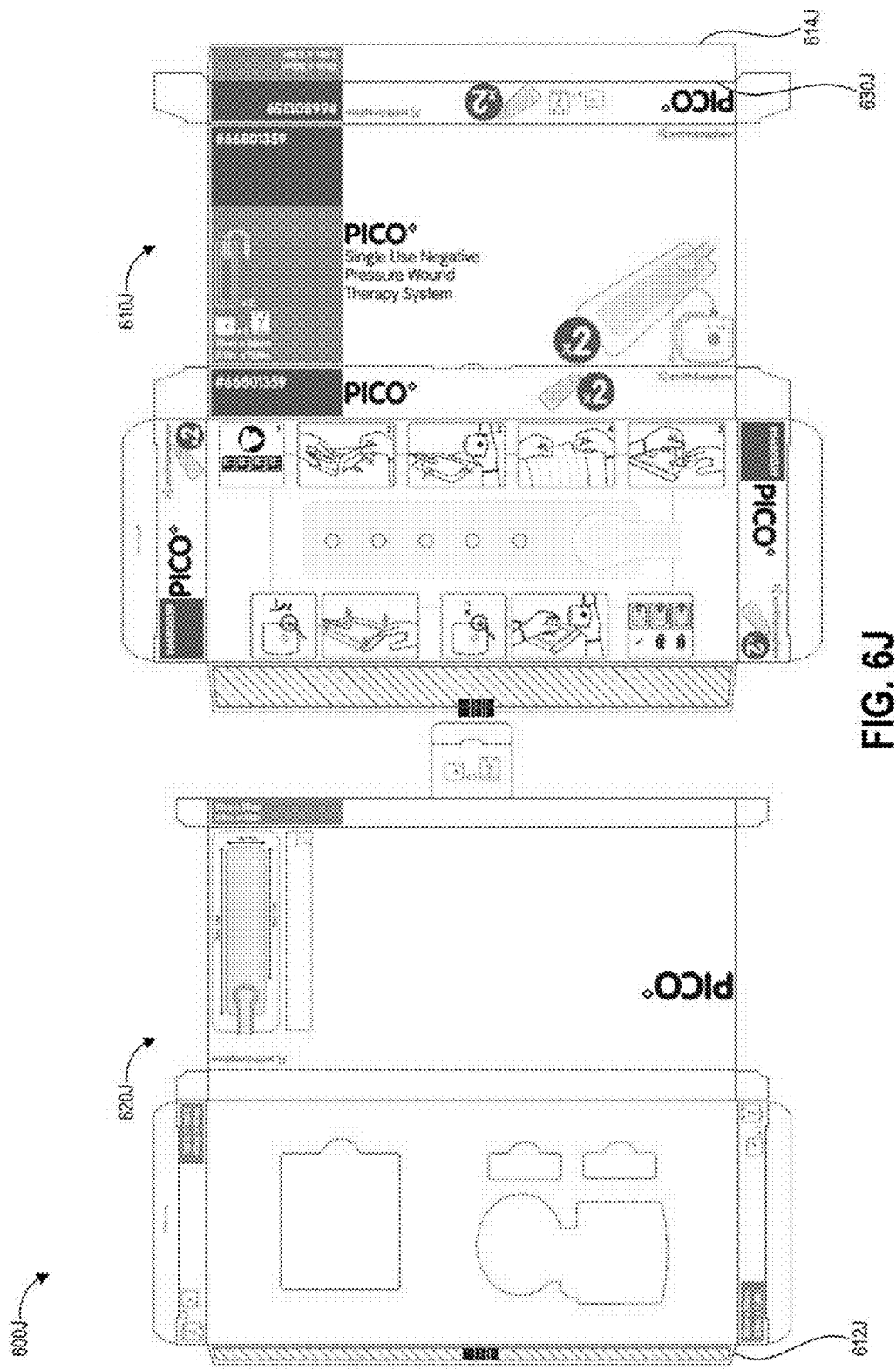
Figure 6K:
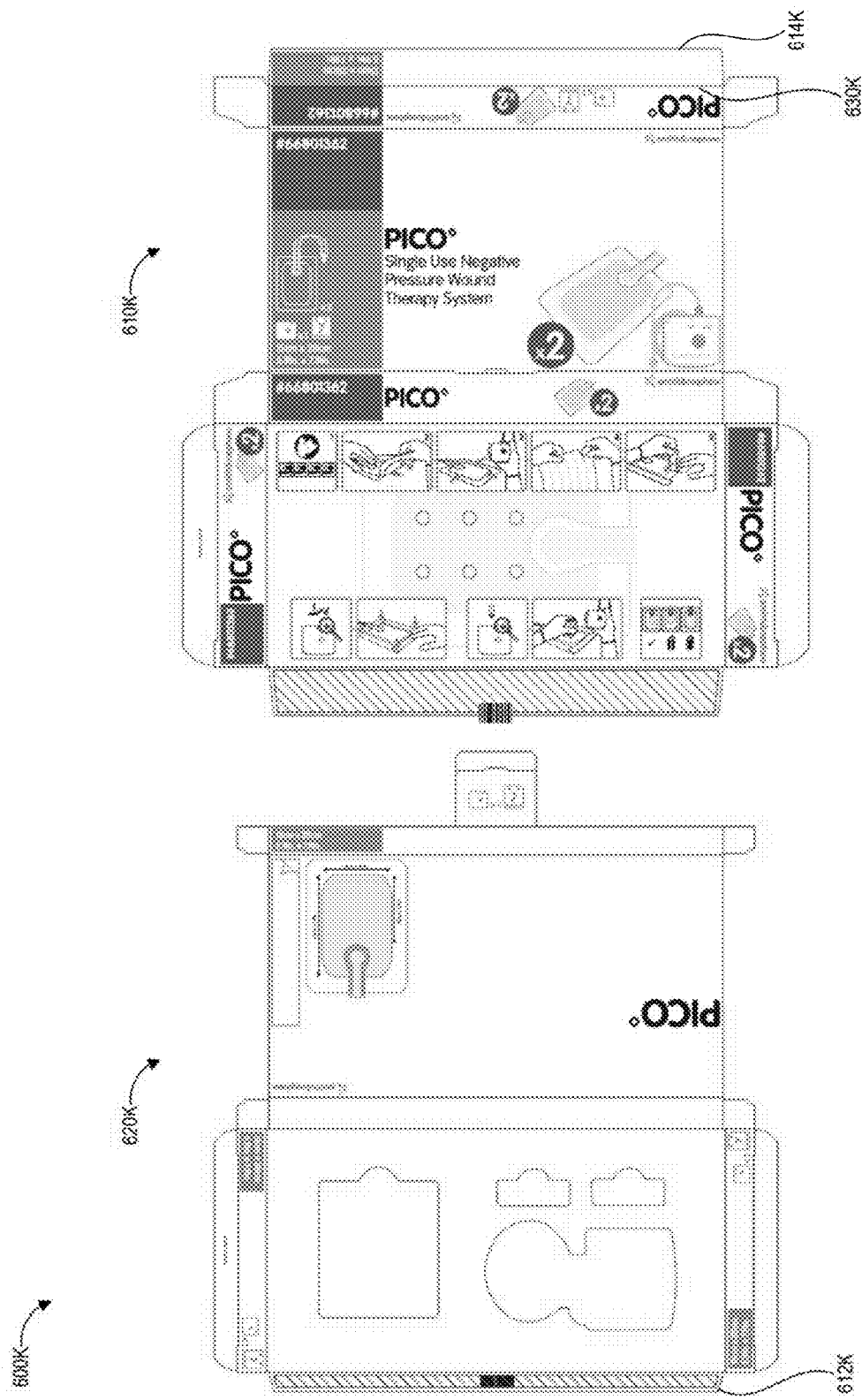
Figure 6L:
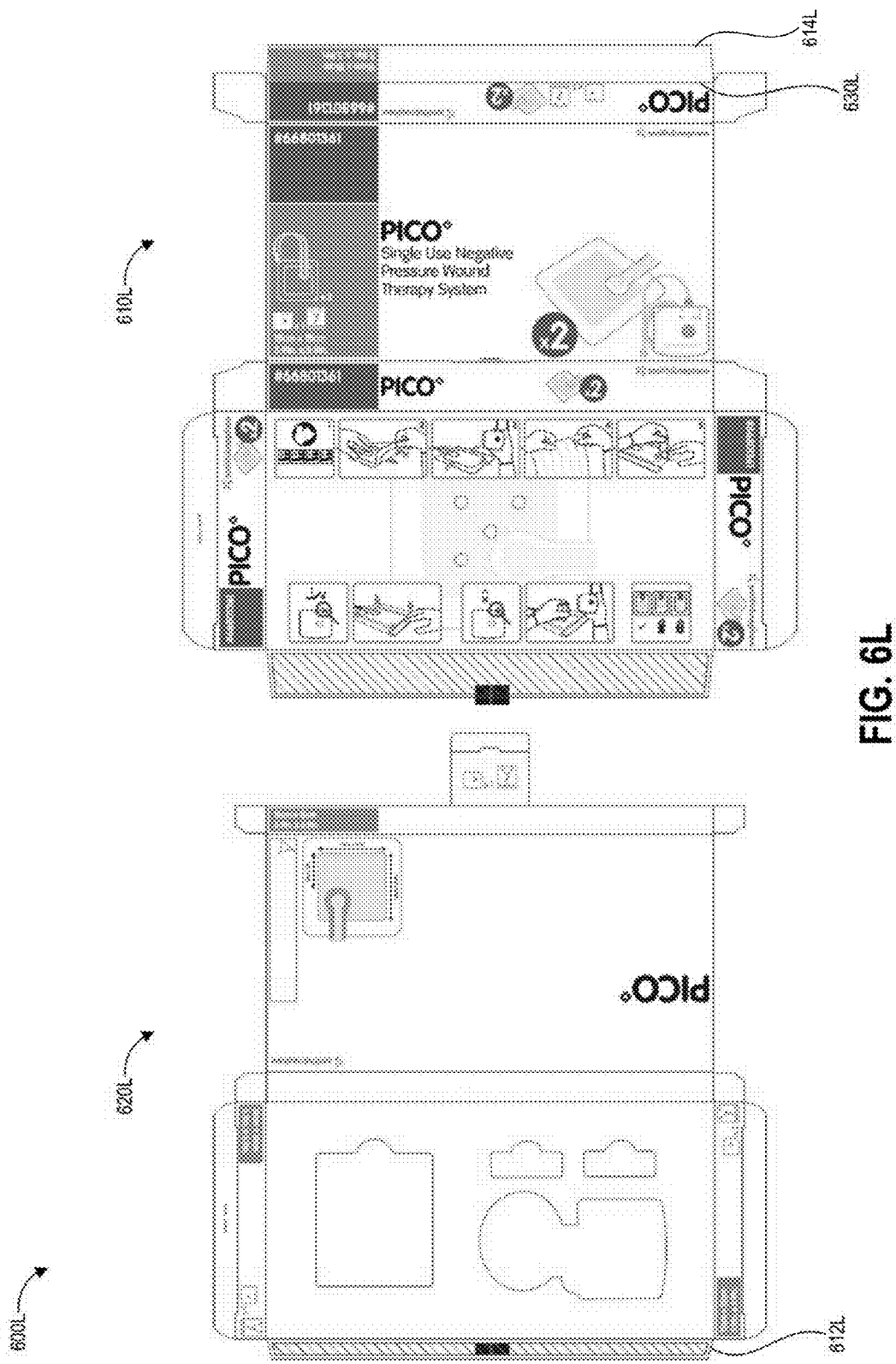
Figure 6M:
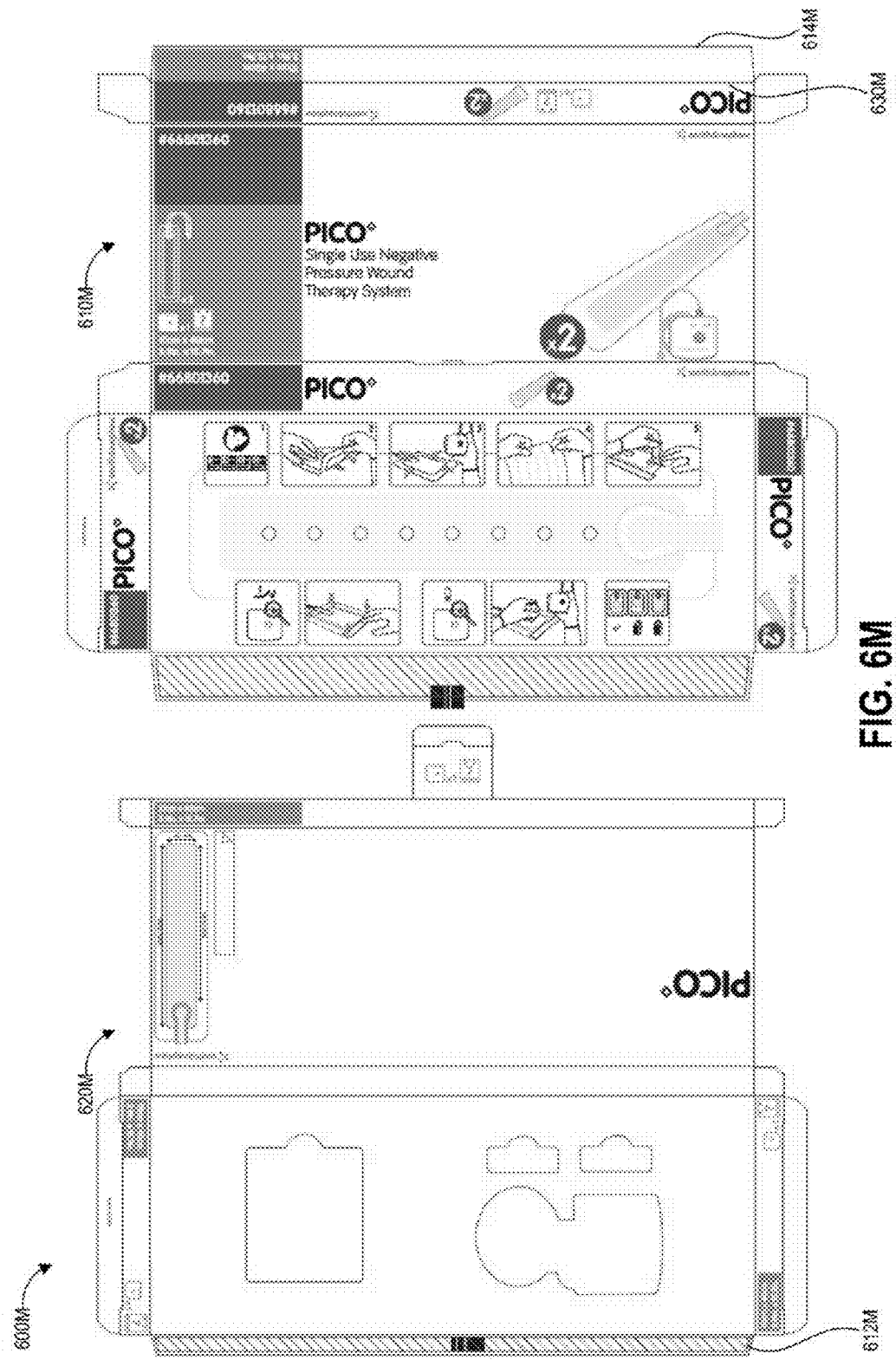
Figure 6N:
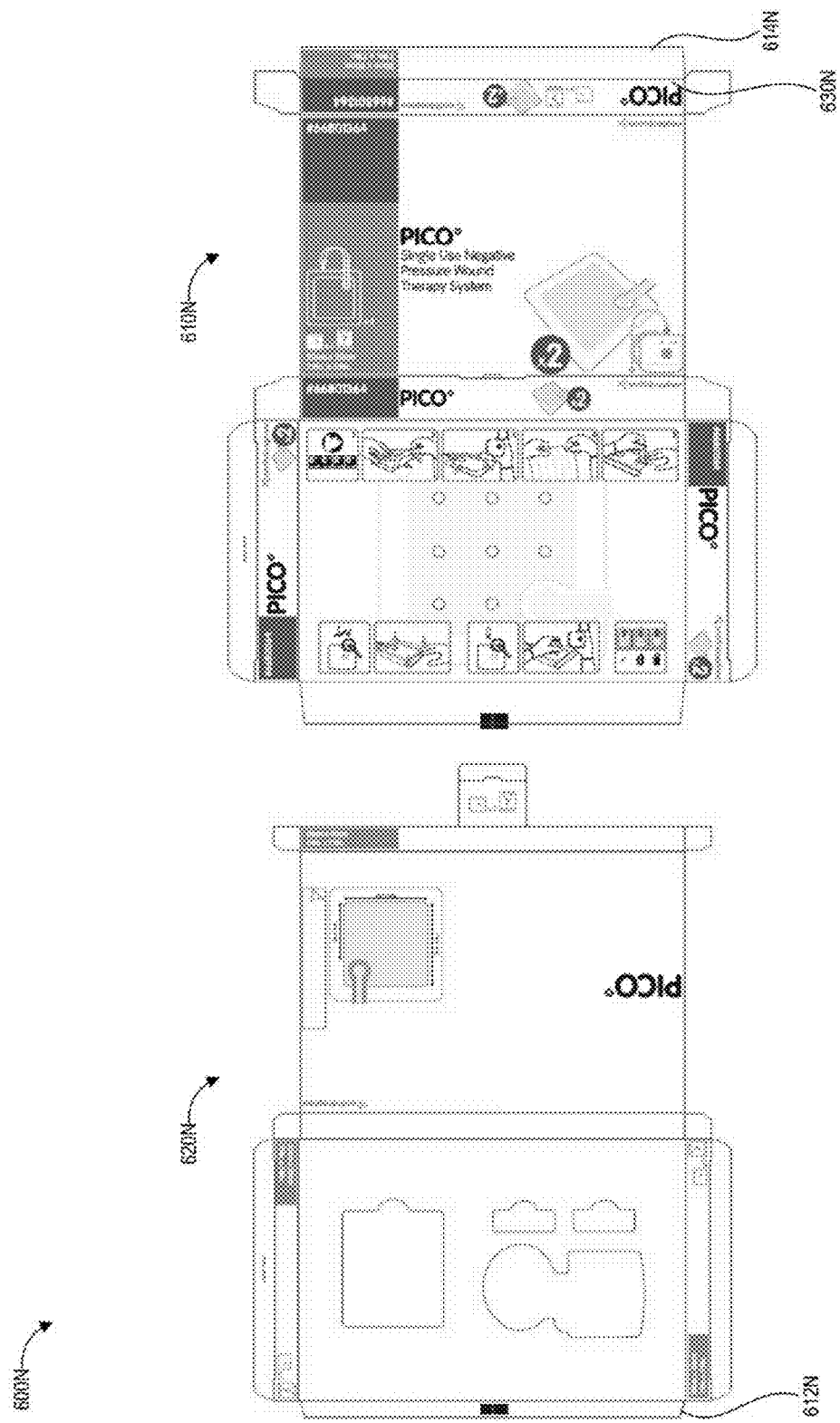
Figure 60:
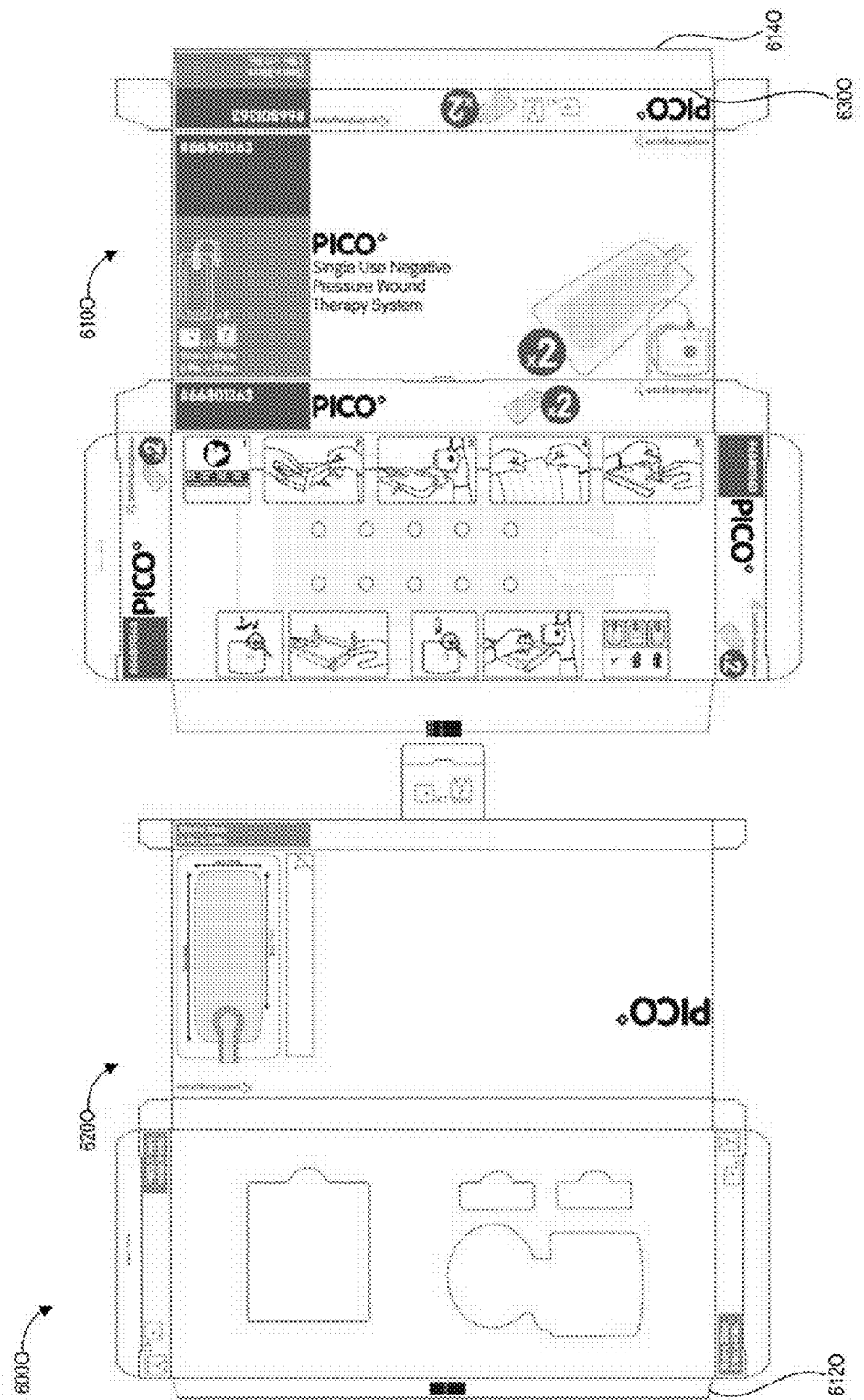
Figure 6P:
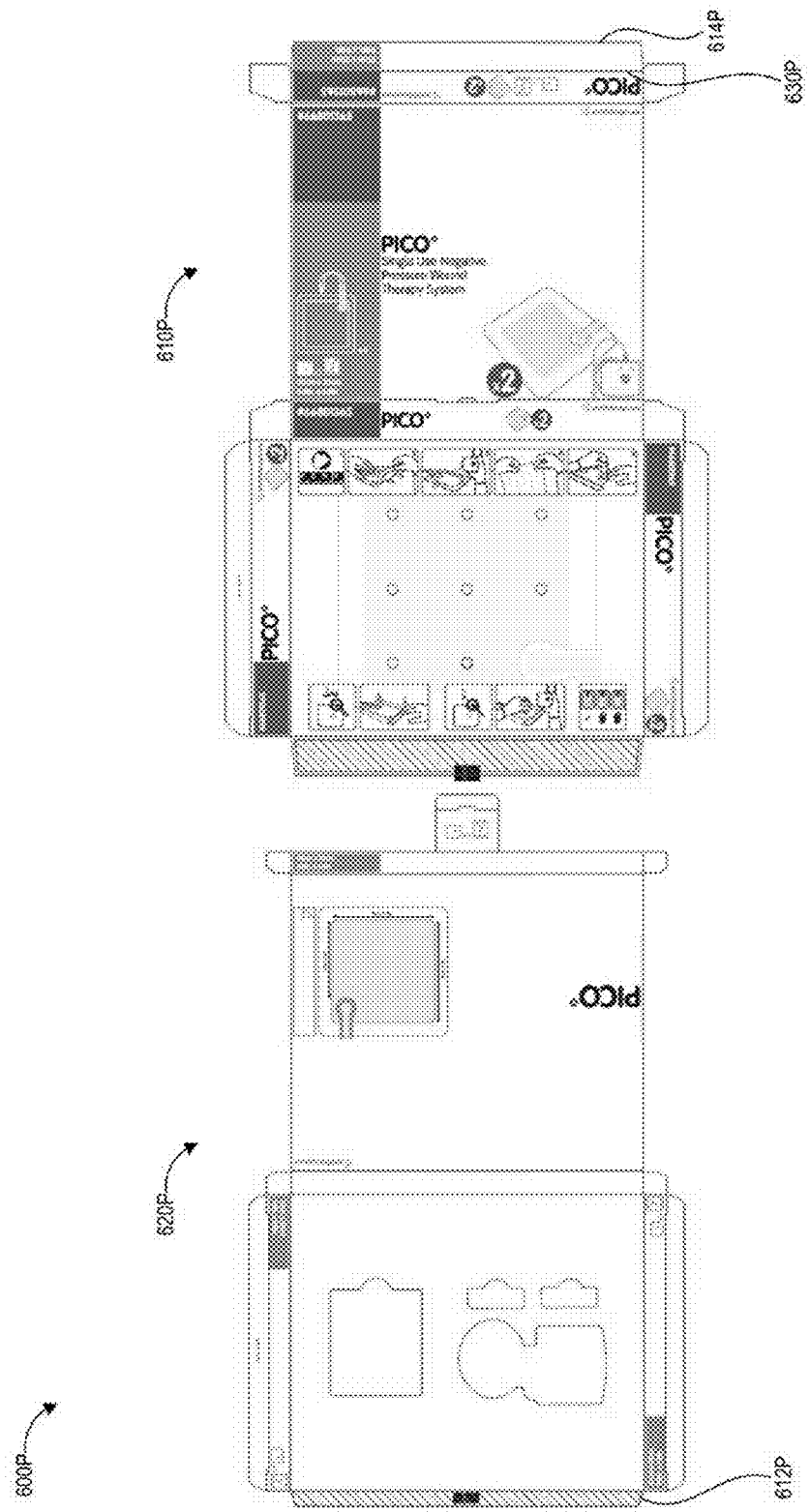

FIGS. 6A-6P illustrate two dimensional sheets adapted to be folded and assembled into book-style carton designs for various reduced pressure wound therapy kit packaging embodiments. FIGS. 6A-6P each illustrate sheet sets for two compartments for the folding carton including fold lines, closure flaps, panels, glue flaps, and a perforated hinge line 630A-630P. FIGS. 6A-6P each illustrate a different artwork embodiment for the dressing compartment 610A-610P and for a surface of the pump compartment 620A-620P that will be the packaging top surface when fully assembled, the artwork indicating a shape and size of dressing stored therein.

FIGS. 6A-6P illustrate the artwork that can be displayed on the upper panel of the dressing compartment 610A-610P depicting the instructions and the dressing, the artwork that can be displayed on the bottom panel of the dressing compartment 610A-610P depicting the packaging contents, the sidewalls that connect the upper panel and bottom panel of the dressing compartment 610A-610P, and glue flaps that will also form some of the sidewalls when the dressing compartment 610A-610P is assembled. FIGS. 6A-6P illustrate the artwork that can be displayed on the bottom panel of the pump compartment 620A-620P depicting dressing dimensions, the shapes of the cut-outs in the upper panel that will form the recesses for receiving and supporting the packaging trays, the sidewalls that connect the upper panel and bottom panel of the pump compartment 620A-620P, and glue flaps that will also form some of the sidewalls when the pump compartment 620A-620P is assembled.

Each of the sheet sets 600A-600P can be folded and glued to create a book-style, two-compartment carton similar to the carton 400 illustrated in FIGS. 4A-4O. Each of the dressing compartment 610A-610P and the pump compartment 620A-620P can be folded and glued or otherwise affixed to create a box for each compartment. The two compartments can be glued or otherwise affixed together using glue flaps 612A-612P, 614A-612P, such that the gluing or affixing means does not interfere with the perforated tear line 630A-630P along the folding hinge between the compartments. It would be in this configuration that the carton would typically be filled with the negative pressure wound therapy system components described above, sealed, and shipped to a consumer. For example, dressing contents can be end loaded into the dressing compartment 610A-610P and the ends sealed by some ordinary method. The pump packaging tray and pump instruction booklet can be placed in the recesses of the pump compartment 620A-620P, the dressing compartment 610A-610P and the pump compartment 620A-620P can be folded together, and the folded packaging carton can be sealed in the folded position, for example by affixing an adhesive closure means to the closure flap between the compartments.

FIG. 6A illustrates an embodiment of packaging designed to contain a single wound dressing in dressing compartment 610A, the wound dressing having for example a dimension of 10 cm×20 cm. FIG. 6B illustrates an embodiment of packaging designed to contain a single wound dressing in dressing compartment 610B, the wound dressing having for example a dimension of 10 cm×30 cm. FIG. 6C illustrates an embodiment of packaging designed to contain a single wound dressing in dressing compartment 610C, the wound dressing having for example a dimension of 10 cm×40 cm. FIG. 6D illustrates an embodiment of packaging designed to contain a single wound dressing in dressing compartment 610D, the wound dressing having for example a dimension of 15 cm×15 cm. FIG. 6E illustrates an embodiment of packaging designed to contain a single wound dressing in dressing compartment 610E, the wound dressing having for example a dimension of 20 cm×20 cm.

FIG. 6F illustrates an embodiment of packaging designed to contain two wound dressings in dressing compartment 610F, each wound dressing having for example a dimension of 10 cm×20 cm. FIG. 6G illustrates an embodiment of packaging designed to contain two wound dressings in dressing compartment 610G, each wound dressing having for example a dimension of 10 cm×20 cm. FIG. 6H illustrates an embodiment of packaging designed to contain two wound dressings in dressing compartment 610H, each wound dressing having for example a dimension of 15 cm×20 cm. FIG. 6I illustrates an embodiment of packaging designed to contain two wound dressings in dressing compartment 610I, each wound dressing having for example a dimension of 20 cm×25 cm. FIG. 6J illustrates an embodiment of packaging designed to contain two wound dressings in dressing compartment 610J, each wound dressing having for example a dimension of 10 cm×30 cm. FIG. 6K illustrates an embodiment of packaging designed to contain two wound dressings in dressing compartment 610K, each wound dressing having for example a dimension of 15 cm×20 cm. FIG. 6L illustrates an embodiment of packaging designed to contain two wound dressings in dressing compartment 610L, each wound dressing having for example a dimension of 15 cm×15 cm. FIG. 6M illustrates an embodiment of packaging designed to contain two wound dressings in dressing compartment 610M, each wound dressing having for example a dimension of 10 cm×40 cm. FIG. 6N illustrates an embodiment of packaging designed to contain two wound dressings in dressing compartment 610N, each wound dressing having for example a dimension of 20 cm×20 cm. FIG. 6O illustrates an embodiment of packaging designed to contain two wound dressings in dressing compartment 6100, each wound dressing having for example a dimension of 15 cm×30 cm. FIG. 6P illustrates an embodiment of packaging designed to contain two wound dressings in dressing compartment 610P, each wound dressing having for example a dimension of 25 cm×25 cm.

It will be appreciated that for any of the embodiments of the packaging described herein, not all of the information provided or printed on the surface of the packaging may be present in all embodiments. Additional information may also be provided.

III. Overview of Example Kit Use

Figure 7A:
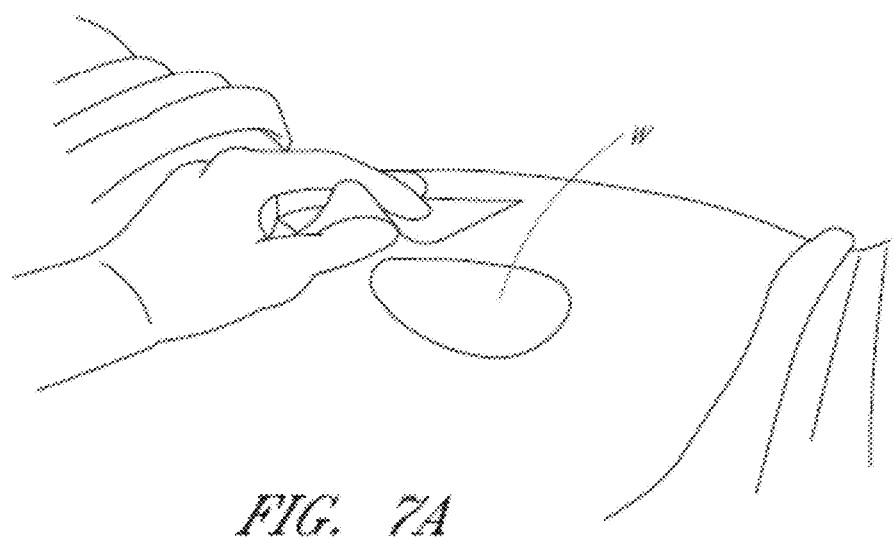
FIGS. 7A-7D illustrate the use of an embodiment of a NPWT wound treatment system being used to treat a wound site on a patient.

FIGS. 7A-7D illustrate the use of an embodiment of a NPWT wound treatment system being used to treat a wound site on a patient. FIG. 7A shows a wound site W being cleaned and prepared for treatment. Here, the healthy skin surrounding the wound site W is preferably cleaned and excess hair removed or shaved. The wound site W may also be irrigated with sterile saline solution if necessary. Optionally, a skin protectant may be applied to the skin surrounding the wound site W. If necessary, a wound packing material, such as foam or gauze, may be placed in the wound site W. This may be preferable if the wound site W is a deeper wound. Such materials can be contained in a detachable preparation materials compartment of a wound therapy kit, and can be sterilized as needed.

Figure 7B:
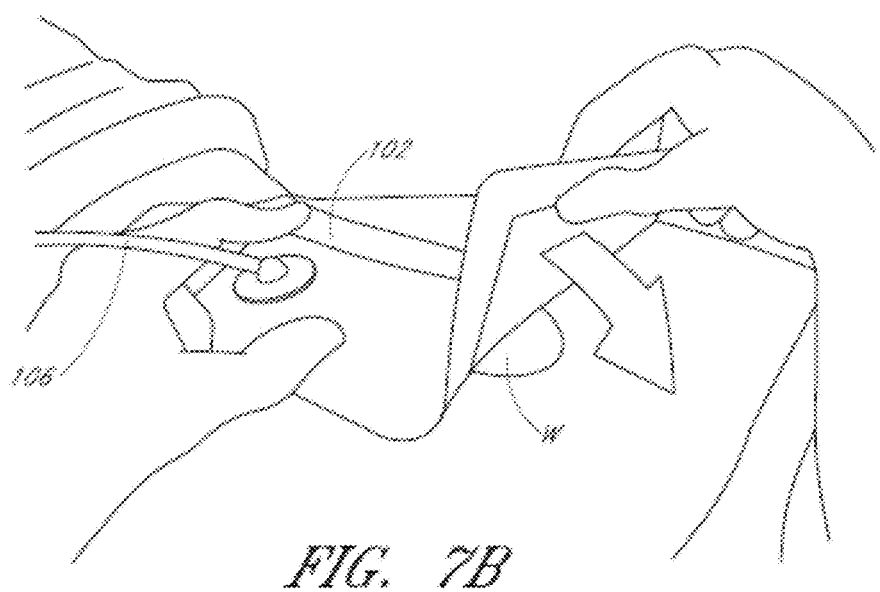

Before or after the skin surrounding the wound site W has been prepared, pump packaging tray can be removed from the pump compartment and the cover can be removed to provide access to the components including pump 104. The dressing 102 can be removed from the dressing compartment and, as illustrated in FIG. 7B, be positioned and placed over the wound site W. The wound dressing 102 can be placed with the wound contact layer of the dressing 102 over and/or in contact with the wound site W. In some embodiments, an adhesive layer can be provided on a lower surface of the wound contact layer, which may in some cases be protected by an optional release layer to be removed prior to placement of the wound dressing 102 over the wound site W. The dressing 102 can be positioned such that the port 108 is in a raised position with respect to the remainder of the dressing 102 so as to avoid fluid pooling around the port 108. In some embodiments, the dressing 102 is positioned so that the port 108 is not directly overlying the wound, and is level with or at a higher point than the wound. To help ensure adequate sealing for TNP, the edges of the dressing 102 can be smoothed over to avoid creases or folds. The tubing 106 can be connected to the dressing 102 either before or after placement of the dressing 102 over the wound.

Figure 7C:
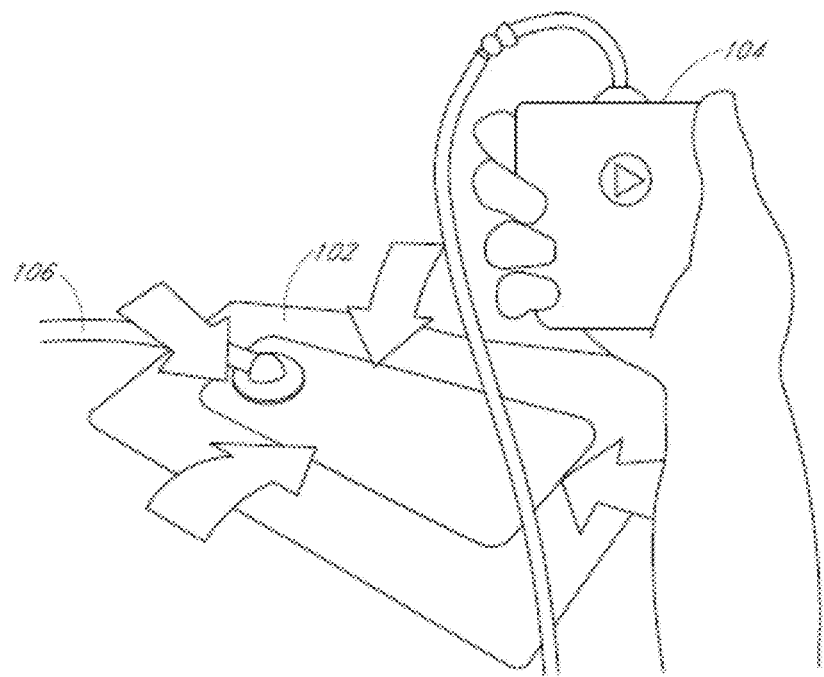

If not already removed from the packaging tray, the pump 104 can be removed from the pump packaging tray and connected to the tubing 106, as illustrated in FIG. 7C. The batteries can be removed from the pump packaging tray and installed in the pump 104 either before or after the pump is attached to the conduit 106. The pump 104 can be configured to apply negative pressure to the wound site via the dressing 102, and typically through the tubing or conduit 106. In some embodiments, a connector may be used to join the conduit 106 to the dressing 102 and to the pump 104. Upon the application of negative pressure with the pump 104, the dressing 102 may in some embodiments partially collapse and present a wrinkled appearance as a result of the evacuation of some or all of the air underneath the dressing 102. In some embodiments, the pump 104 may be configured to detect if any leaks are present in the dressing 102, such as at the interface between the dressing 102 and the skin surrounding the wound site W. Should a leak be found, such leak is preferably remedied prior to continuing treatment. The leak can be remedied by repositioning the dressing 102, smoothing out wrinkles or folds in the dressing, or by applying fixation strips 148 around the periphery of the dressing 102.

Figure 7D:
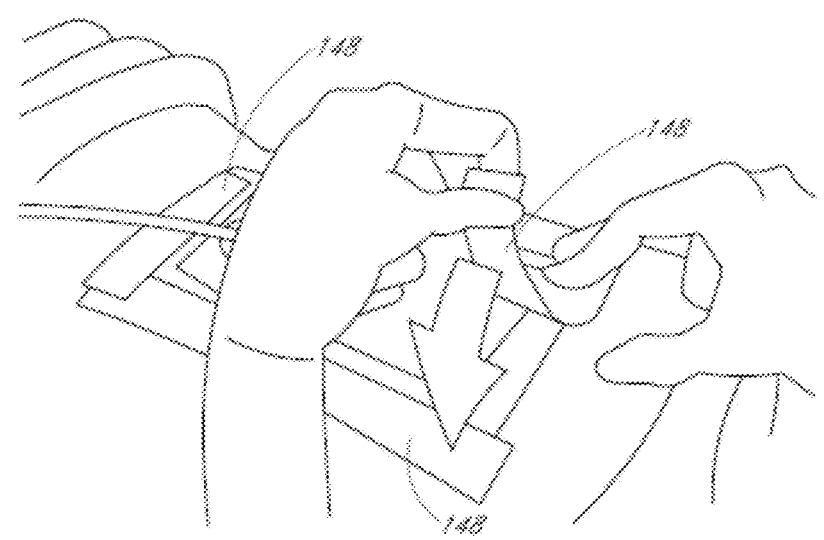

Turning to FIG. 7D, as mentioned, fixation strips 148 can be attached around the peripheral edges of the dressing 102 or otherwise. Such fixation strips 148 can be advantageous in some situations so as to provide additional sealing against the skin of the patient surrounding the wound site W. For example, the sealing or fixation strips 148 can provide additional sealing for when a patient is more mobile. In some cases, the fixation strips 148 may be used prior to activation of the pump 104, particularly if the dressing 102 is placed over a difficult to reach or contoured area. In some embodiments, the dressing kit 100 can be provided with up to five sealing strips.

Treatment of the wound site W preferably continues until the wound has reached a desired level of healing. In some embodiments, it may be desirable to replace the dressing 102 after a certain time period has elapsed, or if the dressing is full of wound fluids. During such changes, the pump 104 may be kept, with just the dressing 102 being changed. Accordingly, the dressing compartment of the kit packaging can be retained together with any unused dressings while the pump compartment may be discarded. The dressing compartment may include printed textual or graphical instructions to assist with dressing changes or provide other information as described above.

IV. Terminology

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A medical device packaging system comprising:
   a first compartment configured to contain a first portion of the device, the first compartment defined by a bottom panel, an upper panel, and at least one sidewall;
   a second compartment configured to contain a second portion of the device, the second compartment defined by a bottom panel, an upper panel, and at least one sidewall;
   a hinge comprising:
      (i) a sheet of material connecting the bottom panel of the first compartment to the bottom panel of the second compartment, and
      (ii) a tear line along an edge of the bottom panel of the second compartment, the tear line comprising a plurality of perforations or weakened lines in the sheet of material to allow removal of the first compartment from the second compartment; and
   instructions for using the medical device provided on an exterior surface of the upper panel of the second compartment; and
   wherein the first compartment is removably connected to the second compartment by the hinge allowing the first compartment and second compartment to be folded together such that the upper panel of the second compartment faces the upper panel of the first compartment; and
   wherein removal of the first compartment from the second compartment along the tear line allows a user to discard the first compartment and retain the second compartment including the instructions for using the medical device.

2. The medical device packaging system of claim 1, wherein the hinge comprises a fold line along an edge of the bottom panel of the first compartment, wherein the fold line is adapted to allow the first compartment and second compartment to be folded apart.

3. The medical device packaging system of claim 1, wherein the instructions provided on the exterior surface of the upper panel of the second compartment are visible when the first compartment and second compartment are folded apart.

4. The medical device packaging system of claim 1, wherein the instructions provided on the exterior surface of the upper panel of the second compartment are concealed when the first compartment and second compartment are folded together.

5. The medical device packaging system of claim 1, wherein the upper panel of the first compartment comprises at least one opening adapted to form a recess for receiving and supporting a tray containing the first portion of the device.

6. The medical device packaging system of claim 5, further comprising the tray containing the first portion of the device.

7. The medical device packaging system of claim 5, wherein the at least one opening in the upper panel of the first compartment is visible when the first compartment and second compartment are folded apart.

8. The medical device packaging system of claim 5, wherein the at least one opening in the upper panel of the first compartment is concealed when the first compartment and second compartment are folded together.

9. The medical device packaging system of claim 1, wherein the first compartment is configured to contain one or more wound dressings and the second compartment is configured to contain a pump.

10. The medical device packaging system of claim 1, wherein the first compartment contains one or more wound dressings and the second compartment contains a pump.

11. The medical device packaging system of claim 1, wherein the width of the hinge equates to the height of the highest sidewall of the first compartment plus the height of the highest sidewall of the second compartment.

12. The medical device packaging system of claim 1, wherein the width of the hinge is sized to accommodate both the first compartment and second compartment, when the two compartments are folded together.

13. A negative pressure wound therapy device packaging system comprising:
 a first compartment defined by a bottom panel, an upper panel, and at least one sidewall, wherein the upper panel comprises at least one opening adapted to form a recess for receiving and supporting a negative pressure pump tray;
 a second compartment sized and shaped to contain a plurality of wound dressings, the second compartment defined by a bottom panel, an upper panel, and at least one sidewall;
 a hinge comprising
  (i) a sheet of material connecting the bottom panel of the first compartment to the bottom panel of the second compartment, and
  (ii) a tear line along an edge of the bottom panel of the second compartment, the tear line comprising a plurality of perforations or weakened lines in the sheet of material to allow removal of the first compartment from the second compartment; and
 instructions for using the negative pressure device provided on an exterior surface of the upper panel of the second compartment;
 wherein the first compartment is removably connected to the second compartment by the hinge_allowing the first compartment and second compartment to be folded together such that the upper panel of the second compartment faces the upper panel of the first compartment; and
 wherein removal of the first compartment from the second compartment along the tear line allows a user to discard the first compartment and retain the second compartment including the instructions for using the negative pressure device together with any unused wound dressings.

14. The negative pressure wound therapy device packaging system of claim 13, wherein the negative pressure pump tray comprises:
 a rim extending around the perimeter of the tray adapted to rest against a portion of an exterior surface of the upper panel of the first compartment, the portion of the exterior surface of the upper panel of the first compartment surrounding the at least one opening; and
 a recessed tray portion extending downwardly from the rim, the recessed tray portion adapted to receive and support at least the negative pressure pump, the recessed tray portion sized and shaped to fit within the at least one opening in the upper panel of the first compartment.

15. The negative pressure wound therapy device packaging system of claim 14, the tray further comprising at least one additional recessed tray portion extending downwardly from the rim and adapted to receive and support at least one battery for the negative pressure pump.

16. The negative pressure wound therapy device packaging system of claim 14, the tray further comprising an additional recessed tray portion extending downwardly from the rim and connected to the recessed tray portion, the additional recessed tray portion adapted to receive and support a length of conduit tubing connected to the negative pressure pump.

17. The negative pressure wound therapy device packaging system of claim 14, further comprising a pump contained in the first compartment and one or more wound dressings contained in the second compartment.

18. The negative pressure wound therapy device packaging system of claim 13, wherein the width of the hinge equates to the height of the highest sidewall of the first compartment plus the height of the highest sidewall of the second compartment.

19. The negative pressure wound therapy device packaging system of claim 13, wherein the width of the hinge is sized to accommodate both the first compartment and second compartment, when the two compartments are folded together.

* * * * *